United States Patent
Chappel et al.

(10) Patent No.: US 12,070,571 B2
(45) Date of Patent: Aug. 27, 2024

(54) DRUG DELIVERY SYSTEM

(71) Applicant: Debiotech S.A., Lausanne (CH)

(72) Inventors: Eric Chappel, Lausanne (CH); Dimitry Dumont-Fillon, Lausanne (CH)

(73) Assignee: DEBIOTECH S.A., Lausanne (CH)

( * ) Notice: Subject to any disclaimer, the term of this patent is extended or adjusted under 35 U.S.C. 154(b) by 901 days.

(21) Appl. No.: 17/056,769

(22) PCT Filed: Jul. 5, 2019

(86) PCT No.: PCT/IB2019/055742
§ 371 (c)(1),
(2) Date: Nov. 19, 2020

(87) PCT Pub. No.: WO2020/012308
PCT Pub. Date: Jan. 16, 2020

(65) Prior Publication Data
US 2021/0213192 A1    Jul. 15, 2021

(30) Foreign Application Priority Data

Jul. 11, 2018 (EP) .................................. 18182850
Dec. 21, 2018 (EP) .................................. 18215745
(Continued)

(51) Int. Cl.
*A61M 5/14*    (2006.01)
*A61M 5/142*   (2006.01)
(Continued)

(52) U.S. Cl.
CPC ...... *A61M 5/1409* (2013.01); *A61M 5/14248* (2013.01); *A61M 5/14593* (2013.01);
(Continued)

(58) Field of Classification Search
CPC ............ A61M 5/1409; A61M 5/14248; A61M 5/155; A61M 5/16881; A61M 5/172;
(Continued)

(56) References Cited

U.S. PATENT DOCUMENTS 1,516,032 A    11/1924   White
3,370,754 A     2/1968   Cook
(Continued)

FOREIGN PATENT DOCUMENTS

EP    1403519 A1    3/2004
GB    2404031       1/2005
(Continued)

OTHER PUBLICATIONS

European Search Opinion dated Jan. 7, 2019 for Application N° EP18182850.0.
(Continued)

*Primary Examiner* — Tasnim Mehjabin Ahmed
(74) *Attorney, Agent, or Firm* — NIXON & VANDERHYE

(57) ABSTRACT

A delivery system configured to be secured on a patient skin which comprises a first container having a first variable volume; a second container having a second variable volume; and a skin adherable unit configured to secure the first container and the second container to the patient skin. The medical device may further comprise a containers' interface configured to operatively couple the first container and the second container such that a volume increase of the second variable volume may induce a volume decrease of the first variable volume. Preferentially, the system further comprises a vent device configured to prevent any unintended pressure increase in the first storage compartment.

18 Claims, 23 Drawing Sheets

(30) Foreign Application Priority Data

| | | | |
|---|---|---|---|
| Jan. 11, 2019 | (EP) | .................................... | 19151323 |
| Jan. 11, 2019 | (EP) | .................................... | 19151324 |
| Jan. 11, 2019 | (EP) | .................................... | 19151325 |
| Feb. 6, 2019 | (EP) | .................................... | 19155800 |
| Feb. 15, 2019 | (WO) | ................. | PCT/IB2019/051237 |

(51) Int. Cl.

| | |
|---|---|
| *A61M 5/145* | (2006.01) |
| *A61M 5/155* | (2006.01) |
| *A61M 5/168* | (2006.01) |
| *A61M 5/172* | (2006.01) |
| *A61M 5/20* | (2006.01) |

(52) U.S. Cl.

CPC ........ *A61M 5/155* (2013.01); *A61M 5/16877* (2013.01); *A61M 5/16881* (2013.01); *A61M 5/172* (2013.01); *A61M 5/2053* (2013.01); *A61M 5/14244* (2013.01); *A61M 2005/14264* (2013.01); *A61M 5/16813* (2013.01)

(58) Field of Classification Search

CPC ............ A61M 5/2053; A61M 5/16813; A61M 5/14593; A61M 5/16877; A61M 5/14244; A61M 2005/14264; A61M 2205/8218

See application file for complete search history.

(56) References Cited

U.S. PATENT DOCUMENTS

| | | | |
|---|---|---|---|
| 3,570,486 A | 3/1971 | Engelsher | |
| 3,626,474 A | 12/1971 | Hammer | |
| 3,923,058 A | 12/1975 | Weingarten | |
| 4,188,949 A | 2/1980 | Antoshkiw | |
| 5,205,820 A | 4/1993 | Kriesel | |
| 5,639,220 A | 6/1997 | Hayakawa | |
| 9,194,383 B2 | 11/2015 | Knobel | |
| 9,833,565 B2 | 12/2017 | Magnenat et al. | |
| 9,872,955 B2 | 1/2018 | Chappel et al. | |
| 9,903,351 B2 | 2/2018 | Gros-d'aillon | |
| 2004/0115068 A1 | 6/2004 | Hansen et al. | |
| 2005/0044964 A1 | 3/2005 | Oskouei et al. | |
| 2006/0069382 A1 | 3/2006 | Pedersen | |
| 2008/0009836 A1* | 1/2008 | Fiering | A61M 5/14276 604/891.1 |
| 2008/0118376 A1 | 5/2008 | Verrilli | |
| 2009/0003515 A1 | 1/2009 | Naidu et al. | |
| 2009/0035152 A1 | 2/2009 | Butterfield | |
| 2011/0118432 A1 | 5/2011 | Zhao et al. | |
| 2011/0132480 A1 | 6/2011 | Chappel | |
| 2012/0048403 A1 | 3/2012 | Chappel et al. | |
| 2012/0186509 A1 | 7/2012 | Milijasevic et al. | |
| 2012/0316492 A1 | 12/2012 | Chappel | |
| 2013/0046253 A1 | 2/2013 | Yavorsky et al. | |
| 2014/0166528 A1 | 6/2014 | Bianchi | |
| 2015/0290389 A1 | 10/2015 | Nessel | |
| 2015/0346732 A1 | 12/2015 | Chappel | |
| 2016/0175515 A1* | 6/2016 | McCullough | A61M 5/20 604/65 |
| 2016/0206811 A1 | 7/2016 | Shih et al. | |
| 2016/0213851 A1 | 7/2016 | Weibel | |
| 2016/0271324 A1 | 9/2016 | Chappel et al. | |

FOREIGN PATENT DOCUMENTS

| | | |
|---|---|---|
| JP | H10-057487 A | 3/1998 |
| JP | 2009-531111 A | 9/2009 |
| JP | 2012-000470 A | 1/2012 |
| WO | WO 2005044343 A1 | 5/2005 |
| WO | WO 2008021252 A1 | 2/2008 |
| WO | WO 2009017487 A1 | 2/2009 |
| WO | WO 2010008675 A1 | 1/2010 |
| WO | WO 2010020891 | 2/2010 |
| WO | WO 2011011814 | 2/2011 |
| WO | WO 2011098867 | 8/2011 |
| WO | WO 2011098946 | 8/2011 |
| WO | WO 2014090745 | 6/2014 |
| WO | WO 2014108860 | 7/2014 |
| WO | WO 2019159121 | 8/2019 |
| WO | WO 2020075042 | 4/2020 |
| WO | WO 2020129002 | 6/2020 |

OTHER PUBLICATIONS

European Search Report dated Jan. 7, 2019 for Application N° EP18182850.0.

International Search Report dated Apr. 23, 2019 for Application N° PCT/IB2019/051237.

International Search Report dated Mar. 19, 2020 for Application N° PCT/IB2019/061189.

International Search Report dated Oct. 23, 2019 for Application N° PCT/IB2019/055742.

Written Opinion of the ISA dated Apr. 23, 2019 for Application N° PCT/IB2019/051237.

Written Opinion of the ISA dated Mar. 19, 2020 for Application N° PCT/IB2019/061189.

Written Opinion of the ISA dated Oct. 23, 2019 for Application N° PCT/IB2019/055742.

Office Action issued in Japanese Patent Application No. 2020-543070 dated Nov. 29, 2022.

Office Action issued in Japanese Patent Application No. 2020-543070 dated Jun. 20, 2023.

Notice of Allowance, issued in U.S. Appl. No. 16/969,201 dated Nov. 1, 2023.

* cited by examiner

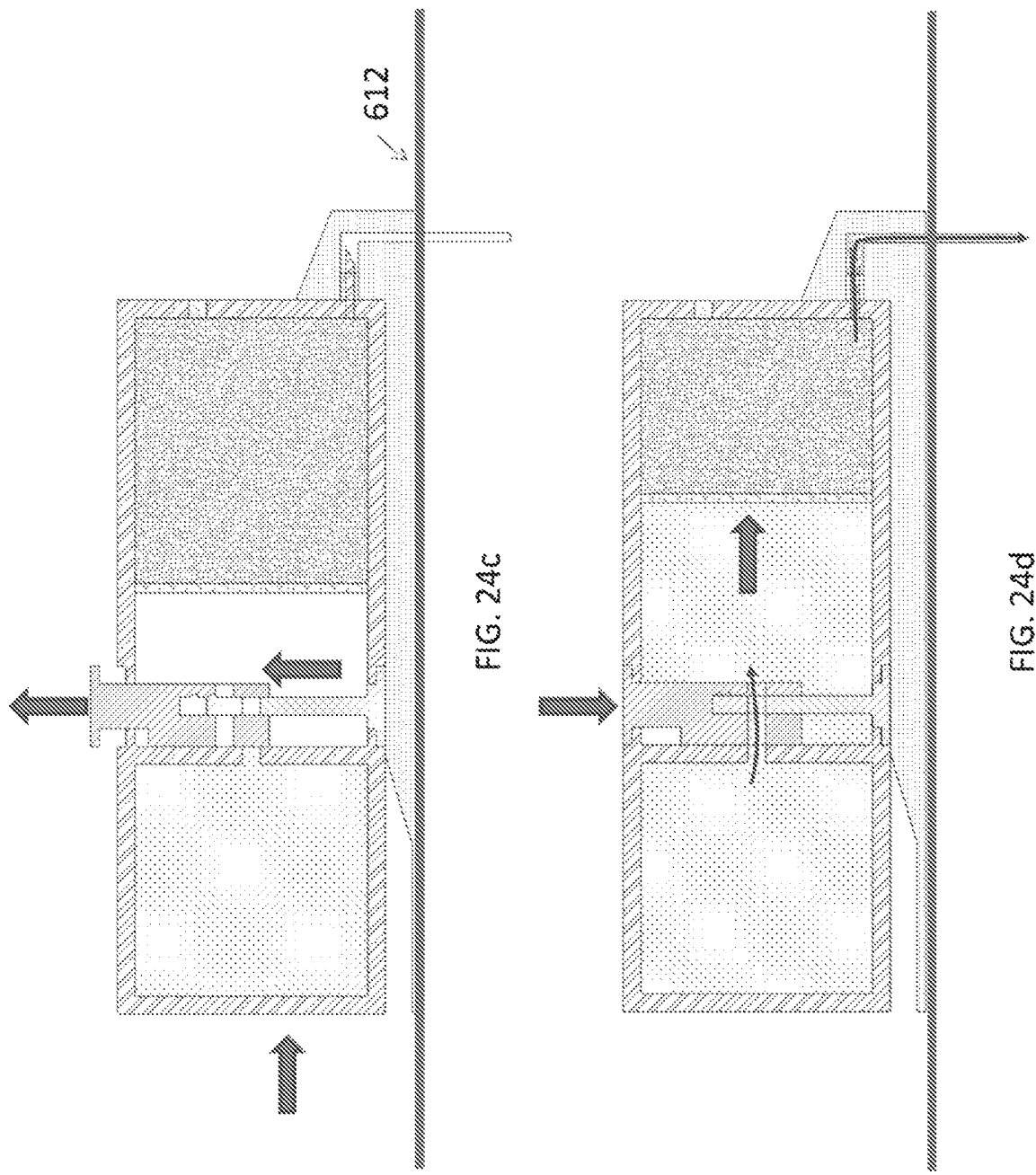

DRUG DELIVERY SYSTEM

CROSS REFERENCE TO RELATED APPLICATIONS

The present application is a United States national stage application of International patent application PCT/IB2019/055742 filed on Jul. 5, 2019 designating the United States, and claims foreign priority to European Patent Application Numbers EP18182850.0 filed on Jul. 11, 2018, EP18215745.3 filed on Dec. 21, 2018, EP19151323.3 filed on Jan. 11, 2019, EP19151324.1 filed on Jan. 11, 2019, EP19151325.8 filed on Jan. 11, 2019, and EP19155800.6 filed on Feb. 6, 2019, and claims also foreign priority to International Patent Application No. PCT/IB2019/051237 filed on Feb. 15, 2019, the contents of all eight (8) documents being herewith incorporated by reference in their entirety.

FIELD OF DISCLOSURE

This disclosure relates to a drug delivery system. In particular, it relates to a drug delivery system which may comprise a drug container and a pressurized means.

STATE OF THE ART

Many kinds of delivery device are available such as pen, jet and other device designed to inject a single or multiple dose of drug contained in a cartridge or reservoir. Depending on the application (acute intervention, prevention or long-term treatment) the intended user is a healthcare professional, a caregiver or the patient himself. The main drawback of these devices is that the duration of the injection must be short because the user has to handle the device for the whole duration of the delivery. This means that the solution cannot be viscous, the volume to be injected has to be low, and/or the flow rate must be within a short range.

For example, while pen injectors are preferred to inject aqueous solutions up to 3 mL, on-body-injectors become desirable in case of viscous solutions and/or large volume of drugs. Furthermore, some specific subcutaneous formulations cannot be injected via a pen injector even if they comprise recombinant human hyaluronidase as excipient to lower the resistance of the tissues during the SC injection. As consequence, there is a growing interest in providing an on-body-injector able to infuse various formulations of drugs or solution.

The bolus delivered by an on-body-injector is usually accomplished by moving a plunger inside a cylindrical barrel filled with the drug (the reservoir being prefilled or filled by the user). Various engines are used to move the plunger: preloaded spring, linear motor, stepper motor, induction motor, . . . Usually, the on-body-injectors are fully disposable thus such devices shall ideally comprise no complex engine.

Another type of on-body-injectors comprises a flexible pouch (storing the drug) pressurized by an elastomeric bladder filled with a propellant. Such devices comprise several drawbacks:
The need of an output valve for the filling to prevent free flow,
The relative large dead volume due to the final collapse of the flexible pouch which is not optimal, notably around the filling port and the outlet port, inducing the presence of air after filling and loss of drug which remains in the soft reservoir after infusion,
The risk of incomplete infusion if the flexible pouch does not collapse in a homogeneous way, and/or
The need of an opening in the device to introduced the filled flexible pouch inside the bladder before infusion.

Such structure of device is more adapted to very large volume of reservoir (typ. 100 ml or more) in order to maintain the dead volume less than 10%, preferentially less than 5%, more preferentially less than 2%. Moreover, the mechanical constraints related to the large bladder area that is pressurized lead to the use of a reinforced and heavy housing and thus it cannot be wearable.

For a wearable device directly secured to the patient skin, there is a need of an alternative device structure that:
optimizes the dead volume,
limits the manipulation (and therefore the risk of errors),
provides a compact solution to infuse volumes ranging from 1 to 60 ml (typ. 5 ml),
provides means to monitor the infusion, and/or
provides passive means to prevent free flow.

GENERAL DESCRIPTION OF THE DISCLOSURE

According to a first aspect of the disclosure, the document describes a delivery system configured to be secured on a patient skin comprising:
a first container having a first movable wall and a first storage compartment intended to store a medical fluid,
a second container having a second movable wall and a second storage compartment, and
a skin adherable unit configured to secure the first container and the second container to the patient skin.

The first movable wall and the second movable wall are facing each other and define a containers' interface having a cavity. The system may further comprises a vent device having a first venting element (such as one or more aperture) configured to allow a pressure equilibration between the cavity of the containers' interface and the outside of the delivery system when at least one of the first movable wall and the second movable wall moves. For example, the vent device may provide access to the fluid surrounding the delivery system which may be the ambient air/gas at the atmospheric pressure. The first venting element may prevent any (unintended) over pressure on the first movable wall caused by a leak or air trapped in the cavity of the containers' interface. The first venting element may be configured to be enabled and/or disabled at a specific time period(s) of use.

The vent device may be configured to prevent any unintended pressure increase in the first storage compartment.

The first movable wall may be configured to change the volume of the first storage compartment. And, the second movable wall may be configured in such a manner that a change of the second storage volume induces a movement of the second movable wall. At least one of the first and second movable walls may comprise a flexible membrane.

At least one of the first storage compartment and the second storage compartment may be initially empty and the volume of the containers' interface cavity may initially be maximal.

At least one of the first container and the second container may comprise a rigid part. Said rigid part may extend along at least one length of at least one of the first container and the second container in at least one dimension.

In the case where a container comprises a flexible membrane and a rigid part, the flexible membrane may be fixed or attached to the rigid membrane in order to provide the storage compartment. It may be fixed or attached for example at its edge. For example, it can be welded e. g. by ultrasonic, laser or thermal sealing methods or by standard mechanical joining methods.

In the case where a container comprises two flexible membranes, a first flexible membrane may be fixed or attached to a second flexible membrane in order to provide the storage compartment. It may be fixed or attached for example at its edge. For example, it can be welded e. g. by ultrasonic, laser or thermal sealing methods or by standard mechanical joining methods.

The delivery system may comprise a housing in which at least a part of at least one of the first container and the second container may be arranged. For example, the delivery system may comprise a housing including a concave internal structure fitted to at least a part of the external surface of at least one of the first container and the second container.

At least one of the housing of the system, the first container, and the second container may comprise a part or a protrusion including the vent device (for example the first venting element or a second venting element as descried thereafter). The protrusion may extend toward the opposite container. And/or, the protrusion may extend along at least a part of the peripheral edge of the container interface cavity.

At least a part of the first container and/or the second container may form a part of the housing of the delivery system.

At least one of the first container and the second container may comprise a concave internal structure in which at least one of the first movable wall and the second movable wall may move or may collapse. Preferentially, the concave internal structure may be a rigid structure and may comprise a rigid internal wall of the storage compartment.

The medical fluid may be an incompressible fluid such as a liquid or a compressible fluid (such as a gas).

Preferentially, the first container and the second container are in pressure communication via the first movable wall and the second movable wall.

In some embodiments, the first container and the second container may be in pressure communication only when the first movable wall and the second movable wall are at least partially in contact.

The cavity of the containers' interface may comprise a variable volume depending on the movement of at least one of the first movable wall and the second movable wall.

Preferentially, the delivery system comprises a third container configured to store a compressed fluid in a third storage compartment. The delivery system may further comprise at least one of a fluid pathway and a fluid communication device (also called valve device) configured to allow fluid communication between the third storage compartment and the second storage compartment when the fluid communication device is in an open state (also called thereafter second position). Preferentially, the fluid communication device further comprises a closed state (also called thereafter first position) configured to prevent the fluid communication between the third storage compartment and the second storage compartment.

In order to prevent any (unintended) pressure increase into the second storage compartment, the vent device may comprise a second venting element (such as one or more aperture) configured to allow a pressure equilibration between the second storage compartment and the outside of the delivery system. As described above, the vent device may provide access to the fluid surrounding the delivery system (outside of the delivery device) which may be the ambient air/gas at the atmospheric pressure. For example, the second venting element may prevent any over pressure in the second storage compartment during the storage time period, caused by leakage of the compressed gas from the third container. The second venting element may be configured to prevent any unintended pressure increase in the first storage compartment due to an (unintded) increase of at least one of the third variable volume and the second variable volume.

The second venting element may be configured to be enabled and/or disabled at a specific time period(s) of use. For example, the second venting element may be disabled (occluded/closed) during the infusion, at the time of the activation of the infusion or (just) before the transition of the fluid communication device from the first position (closed state) to the second position (open state).

In some embodiments, the vent device (for example at least one of the first venting element and the second element) and the fluid communication device may be operatively coupled. For example, the delivery system may further comprise a control device arranged to close the second venting element when the fluid communication device is open. The control device may comprise at least one of an electronic element and a mechanical element.

Before the activation of the delivery device, the second venting element may provide a pressure equilibration of the second storage and outside of the delivery device (the vent device is, this case, enabled), but when the delivery device is activated, the second venting element is preferentially disabled (for example: automatically closed, clogged or occluded) in order to insure a pressure increase into the second storage compartment in such a manner the second movable wall moves toward the first movable causing the solution to flow.

At the end of the solution delivery, the second venting element (or another device) may be enabled or open in order to discharge the pressure (in the second storage compartment) to the outside.

The delivery system may further comprise a triggering device operable coupled with the fluid communication device and configured to change the status or position of the fluid communication device. The delivery system may further comprise a countdown mechanism configured to activate the triggering device after a predetermined time period.

The delivery system may further comprise a transcutaneous device which is in fluid communication with an outlet of the first storage compartment.

The delivery system may further comprise a valve device which is in fluid communication with an outlet of the first storage compartment.

The delivery system may further comprise a hydrophobic membrane which is in fluid communication with an outlet of the first storage compartment. The hydrophobic membrane may cover the outlet of the first storage compartment.

The delivery system may further comprise a flow restrictor which is in fluid communication with an outlet of the first storage compartment.

The delivery system may further comprise a first status indicator (for example an infusion status indicator as described thereafter) which is in fluid or pressure communication with an outlet (for example) of the first storage compartment.

The delivery system may comprise a second status indicator (for example a filling indicator as described thereafter) which is in fluid or pressure communication with the first storage compartment or the cavity between both flexible membranes.

The delivery system may further comprise a pressure transducer which is in fluid communication with an outlet of the first storage compartment.

Preferentially, the delivery system is configured to be used only once or be non reusable, for example, the third container cannot be refilled, the fluid communication once opened cannot be closed, the valve device cannot be moved at it initial state, . . . Preferentially, the delivery system is configured to infuse the whole content of the first container as a single bolus.

According to a second aspect of the disclosure, the document further describes a delivery system configured to be secured on a patient skin comprising:
- a first container having a first flexible membrane and a first variable storage compartment intended to store a medical fluid,
- a second container having a second variable storage compartment,
- a skin adherable unit configured to secure the first container and the second container to the patient skin, and
- a housing having a first cavity.

The first container is at least partially arranged into the first cavity.

The delivery system further comprises a vent device configured to vent the first cavity and a second flexible membrane having a first side configured to be at least partially in contact with the first flexible membrane in delivery condition. The second variable storage compartment is arranged on another side of the second flexible membrane.

Preferentially, the delivery system is configured to be used only once or be non reusable, for example, the third container cannot be refilled, the fluid communication once opened cannot be closed, the valve device cannot be moved at it initial state, . . . Preferentially, the delivery system is configured to infuse the whole content of the first container as a single bolus.

According to a third aspect of the disclosure, the document describes a delivery system configured to be secured on a patient skin comprising:
  A medical device including:
    a first container having a first storage compartment intended to store a medical fluid and having a first variable volume,
    a second container having a second storage compartment having a second variable volume,
    a third container having a third storage compartment configured to store a propellant, and
  a skin adherable unit configured to secure the medical device to the patient skin.

The medical device further comprises a containers' interface configured to operatively couple the first container and the second container such that a volume increase of the second variable volume may induce a volume decrease of the first variable volume.

The containers' interface may be defined by a first wall of the first container and a second wall of the second container.

The first wall may comprise a first movable wall, for example, a first flexible membrane. The second wall may comprise a second movable wall, for example, a second flexible membrane.

The containers' interface may comprise a cavity which may be vented by a first venting element. The first venting element may be configured to allow a pressure equilibration between the cavity of the containers' interface and the outside of the delivery system when at least one of the first variable volume and the second variable volume change. For example, the first venting element may provide access to the fluid surrounding the delivery system which may be the ambient air/gas at the atmospheric pressure.

The second container may comprise a second venting element configured to vent the second storage compartment. The second venting element may be configured to allow a pressure equilibration between the second storage compartment and the outside of the delivery system. For example, the second venting element may provide access to the fluid surrounding the delivery system which may be the ambient air/gas at the atmospheric pressure.

The delivery system may comprise a first valve device configured to occlude the second venting element.

The delivery system may comprise a fluid pathway configured to provide fluid communication between the third storage compartment and the second storage compartment. The delivery system may comprise a second valve device having a first position configured to close the fluid pathway and a second position configured to open the fluid pathway. The delivery system may comprise a trigger device configured to change the position of the second valve device.

In some embodiments, the first valve device and the second valve device may be operatively coupled such that:
  when the first valve device does not occlude the second venting element, the second valve device is in the first position (closed position) (at least before the activation of the infusion),
  when the first valve device does not occlude the second venting element, the trigger device is not in operating condition, for example, it cannot change the position of the second valve device
  when the first valve device occludes (at least partially) the second venting element, the trigger device is in operating condition, for example, it can and is ready to change the position of the second valve device,
  when the first valve device occludes (at least partially) the second venting element, the second valve device may be (optionally automatically) moved from the first position (closed position) to the second position (open position), and/or
  when the first valve device occludes (at least partially) the second venting element, the second valve device is automatically moved from the first position (closed position) to the second position (open position).

In some embodiments, the skin adherable unit comprises a cradle unit configured to be secured on the patient skin and to (removably—optional) receive the medical device. The medical device may comprise a first position where the medical device is not fixed to the cradle unit and a second position where the medical device is fixed to the cradle unit.

In some embodiments, the skin adherable unit may be operatively coupled with at least one of the first valve device and the second valve device such that:
  when the medical device is in a first position, the first valve device does not occlude the second venting element,
  when the medical device is in a first position, the trigger device is not in operating condition, for example, it cannot change the position of the second valve device
  when the medical device is in a second position, the first valve device occludes (at least partially) the second venting element,
  when the medical device is in a second position, the trigger device is in operating condition, for example, it can and is ready to change the position of the second valve device, when the medical device is in a second position, the second valve device may be (optionally automatically) moved from the first position (closed position) to the second position (open position), and/or when the medical device is in a second position, the second valve device is automatically moved from the first position (closed position) to the second position (open position).

Preferentially, the delivery system is configured to be used only once or be non reusable, for example, the third container cannot be refilled, the fluid communication once opened cannot be closed, the valve device cannot be moved at it initial state, . . . Preferentially, the delivery system is configured to infuse the whole content of the first container as a single bolus.

According to a fourth aspect of the disclosure, the document describes a delivery system configured to deliver medical fluid to a patient; The system may comprise at least one of:

a medical device including:
  a first container having a first storage compartment intended to store the medical fluid and having first a variable volume,
  a second container having a second storage compartment having a second a variable volume,
  a third container having a third storage compartment configured to store a propellant, and
a skin adherable unit configured to secure the medical device to the patient skin.

The delivery system may further comprise a first valve device having:
  a first position configured to prevent fluid communication between the second storage compartment and the third storage compartment and
  a second position configured to allow fluid communication between the second storage compartment and the third storage compartment such that the propellant stored in the third storage compartment may flow to the second storage compartment so as to increase the second variable volume.

The medical device may further comprise a containers' interface configured to operatively couple the first container and the second container such that a volume increase of the second variable volume may induce a volume decrease of the first variable volume.

Preferentially, the system further comprises a vent device configured to prevent any unintended pressure increase in the first storage compartment.

The containers' interface may comprise a first movable wall of the first container and a second movable wall of the second container. At least one of the first movable wall and the second movable wall may comprise a flexible membrane. The containers' interface may comprise a cavity defined by at least the first and the second movable wall.

The cavity of the containers' interface may comprise a third variable volume. The vent device may comprise a first venting element configured to allow a pressure equilibration between the cavity of the containers' interface and the outside of the delivery.

The vent device may comprise a second venting element second venting element configured to allow a pressure equilibration between the second storage compartment and the outside of the delivery.

At least one of the first venting element and the second venting element may be configured to prevent any unintended pressure increase in the first storage compartment due to an (unintended) increase of at least one of the third variable volume and the second variable volume.

In some embodiments, the system comprises a second valve device configured to occlude at least partially the second venting element. The first valve device and the second valve device may be operatively coupled such that:
  when the second valve device does not occlude the second venting element, the first valve device is in the first position,
  when the second valve device occludes the second venting element, the first valve device may be moved from the first position to the second position, and/or
  when the second valve device occludes the second venting element, the first valve device is automatically moved from the first position to the second position.

In some embodiments, the system comprises a trigger device configured to change the position of the first valve device. The second valve device and trigger device may be operatively coupled such that:
  when the second valve device does not occlude the second venting element, the trigger device is not in operating condition, and/or
  when the second valve device occludes the second venting element, the trigger device is in operating condition.

In some embodiments, the medical device may comprise a first position and a second position. The medical device may be operatively coupled to at least one of the first valve device, the second valve device, the trigger device, and the skin adherable unit such that:
  when the medical device is in a first position, the second valve device does not occlude the second venting element,
  when the medical device is in a first position, the trigger device is not in operating condition,
  when the medical device is in a second position, the second valve device occludes the second venting element,
  when the medical device is in a second position, the trigger device is in operating condition,
  when the medical device is in a second position, the first valve device may be moved from the first position to the second position, and/or
  when the medical device is in a second position, the first valve device is automatically moved from the first position to the second position.

The position of the medical device may be a position relative to the skin adherable unit (as the cradle unit described in this document) or to the patient skin or to the infusion site. The second position may be required for the infusion, for example, the second position may be the position of the medical system when the medical system is secured on the patient skin and/or ready to use and/or for infusion. The first position may be required during the filling of the first container or all other position before the medical device has been secured on the patient skin.

Preferentially, the delivery system is configured to be used only once or be non reusable, for example, the third container cannot be refilled, the fluid communication once opened cannot be closed, the valve device cannot be moved at it initial state, . . . Preferentially, the delivery system is configured to infuse the whole content of the first container as a single bolus.

LIST OF FIGURES

The present disclosure will be better understood at the light of the following detailed description which contains non-limiting examples illustrated by the following figures.

FIGS. 4a, 4b, 4c, and 4d show schematic views of different housings and/or arrangements.

FIGS. 5a, 5b, 5c, 5d, 5e, 5f and 5g show schematic views of different containers' interfaces.

FIGS. 6a, 6b, 6c, 6d and 6e show schematic views of different status of the delivery system.

Figure 7A:
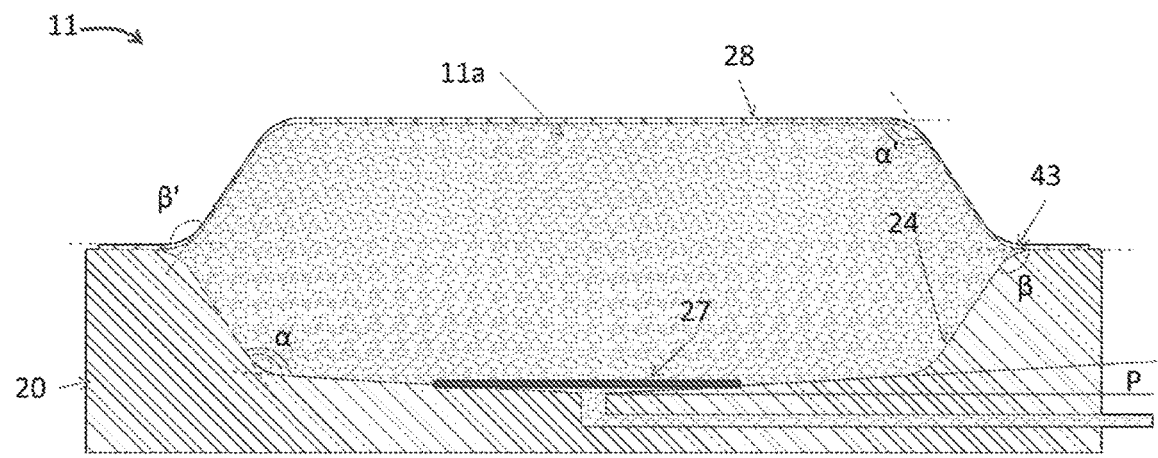
Figure 7B:
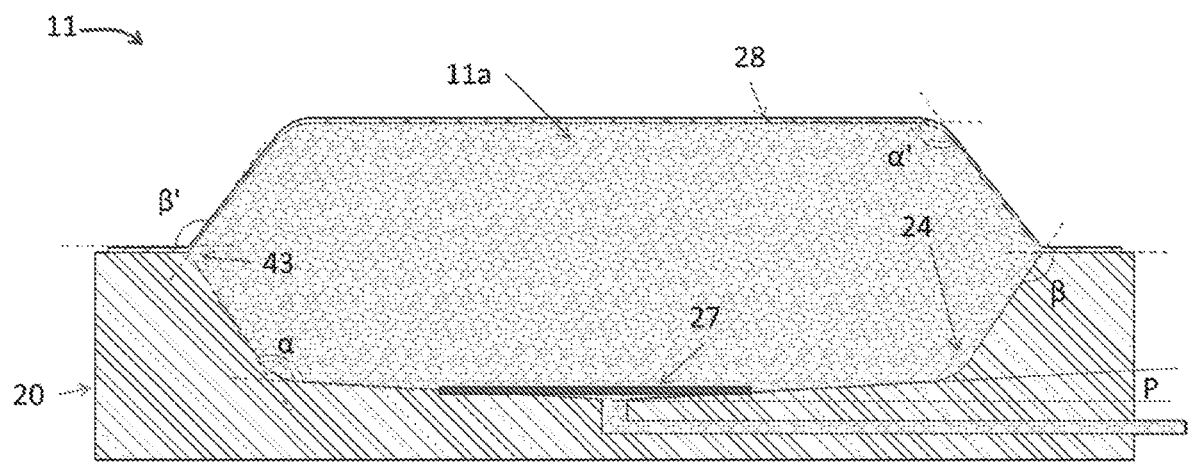

FIGS. 7a and 7b show sectional views of alternative realization modes of a container.

Figure 8:
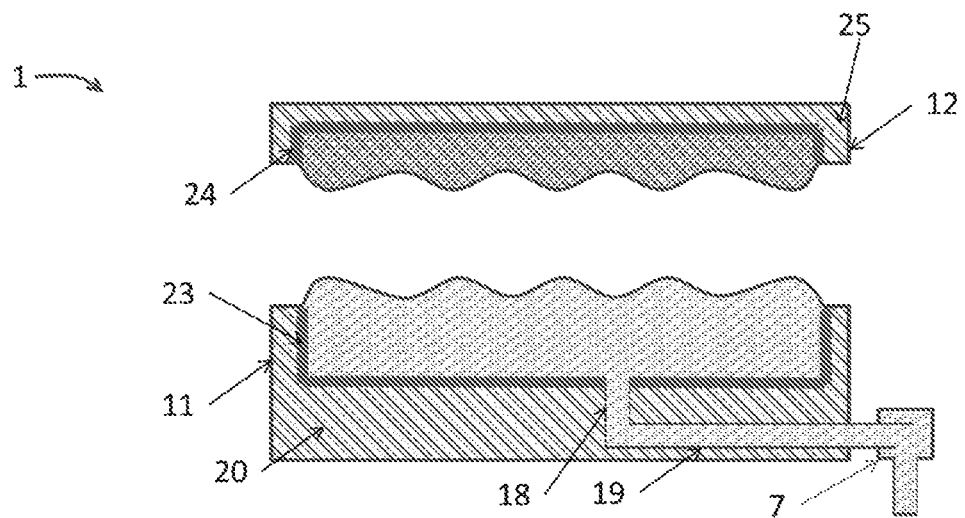

FIG. 8 shows a sectional and exploded view of the first and second containers.

Figure 9:
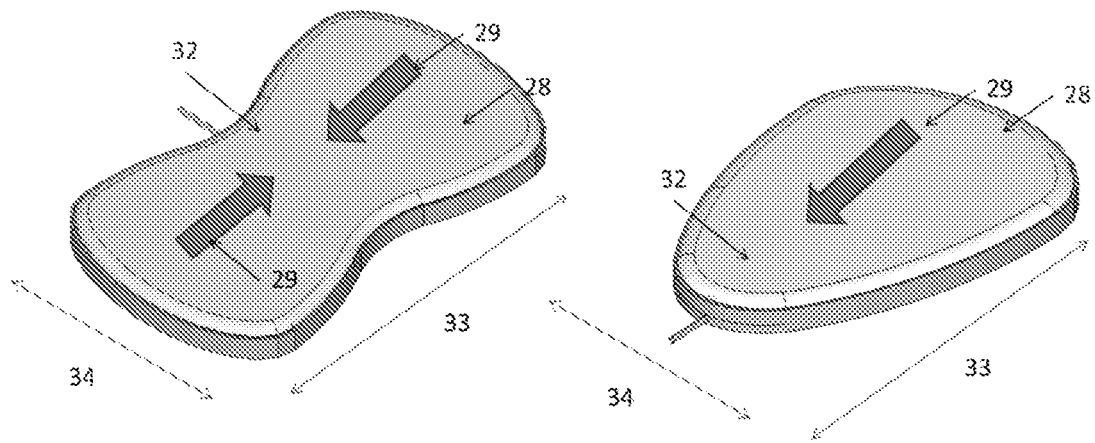

FIG. 9 shows two potential embodiments of the first container.

Figure 10:
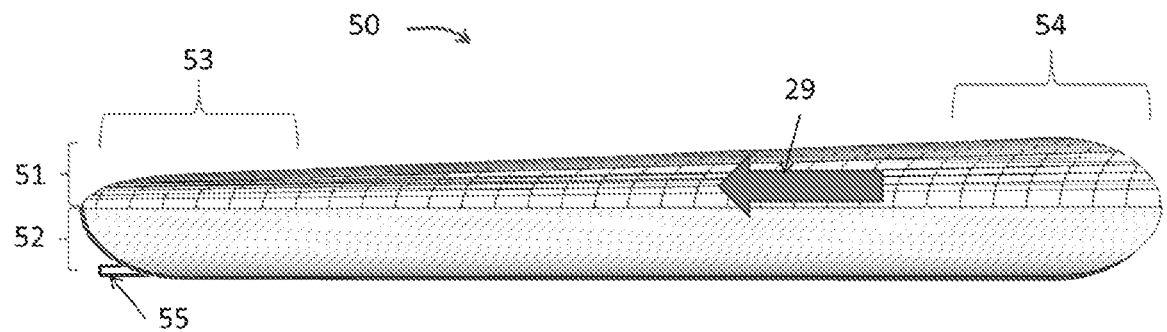

FIG. 10 shows a potential embodiment of the first or second container.

Figure 11:
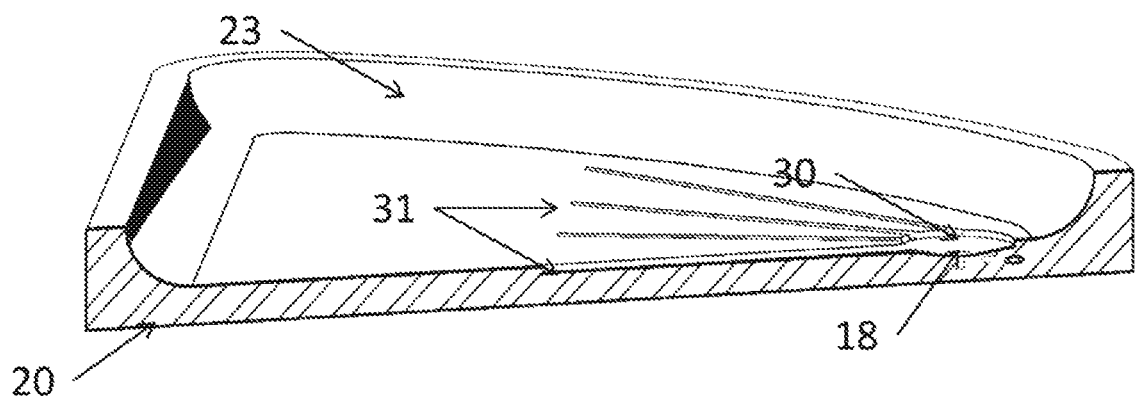

FIG. 11 shows a potential embodiment of a container.

FIGS. 12a, 12b, 12c, and 12d show different sectional views of an embodiment.

Figure 13:
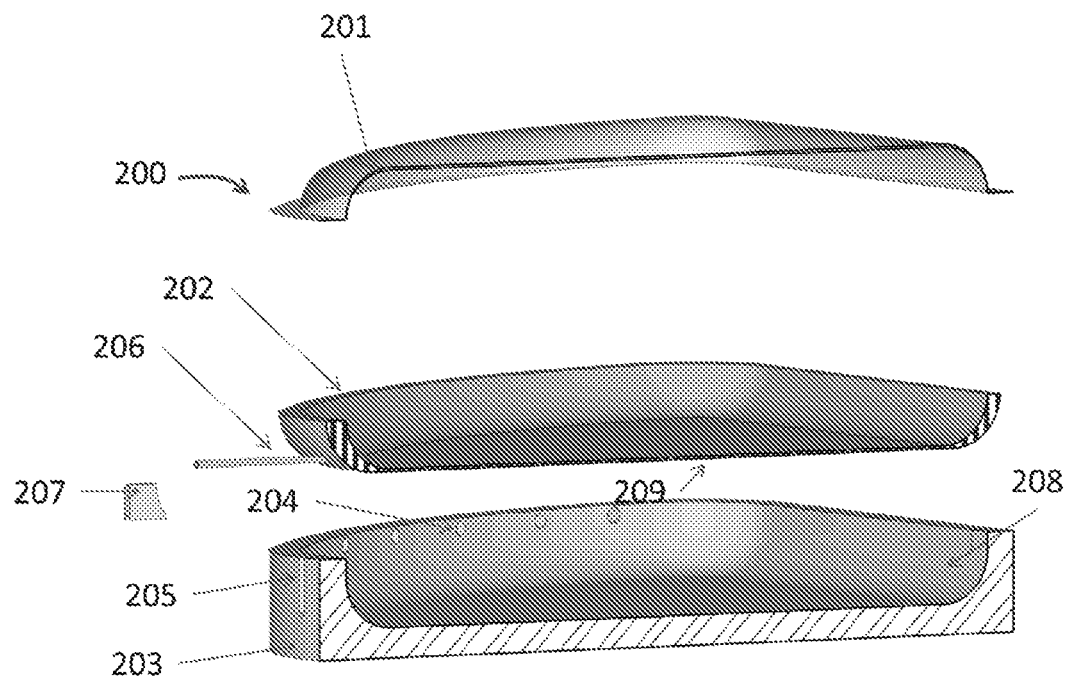

FIG. 13 shows a sectional and exploded view of a potential embodiment of a container.

Figure 14:
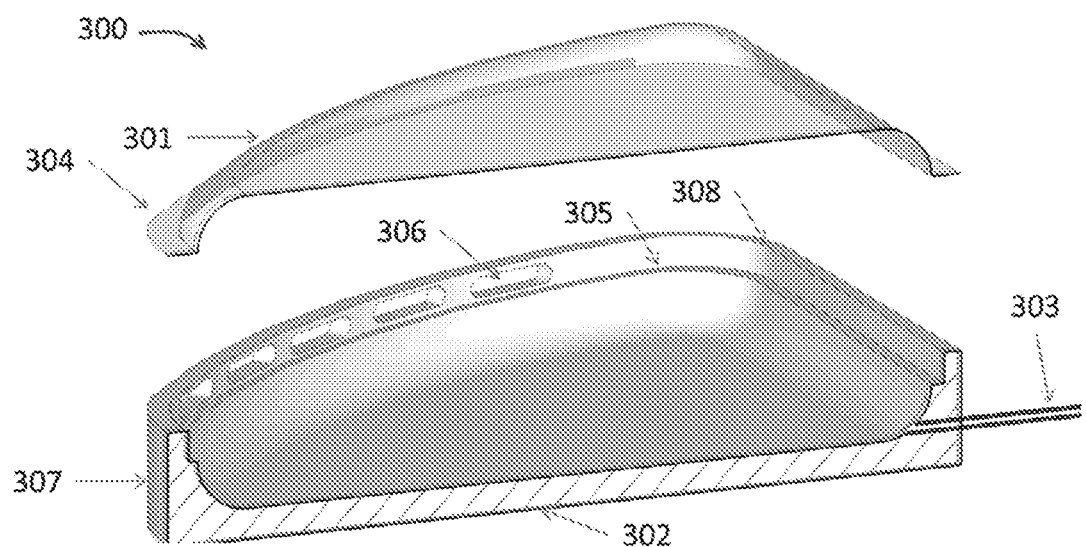

FIG. 14 shows a sectional and exploded view of a potential embodiment of a container.

Figure 15A:
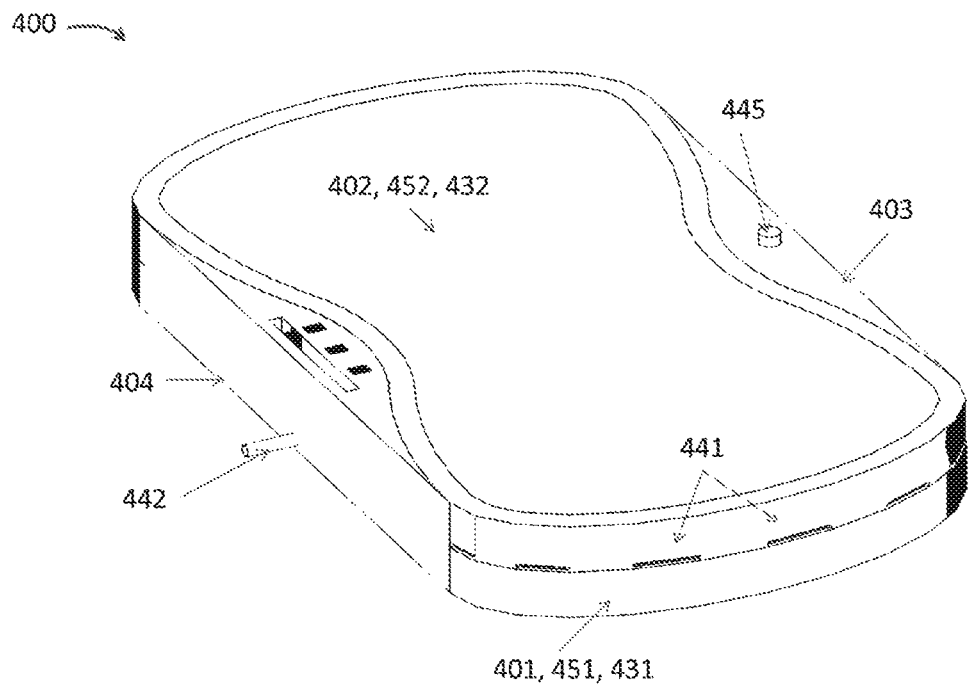
Figure 15B:
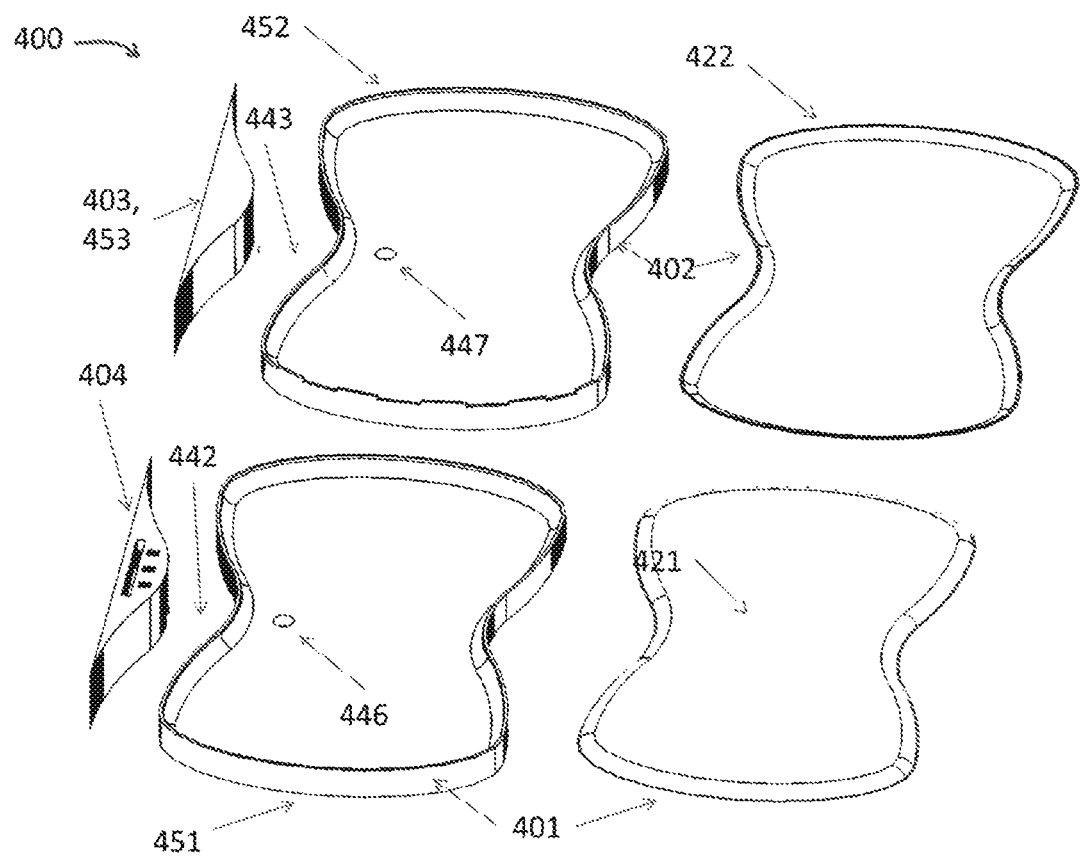

FIGS. 15a and 15b show different views of an embodiment.

Figure 16A:
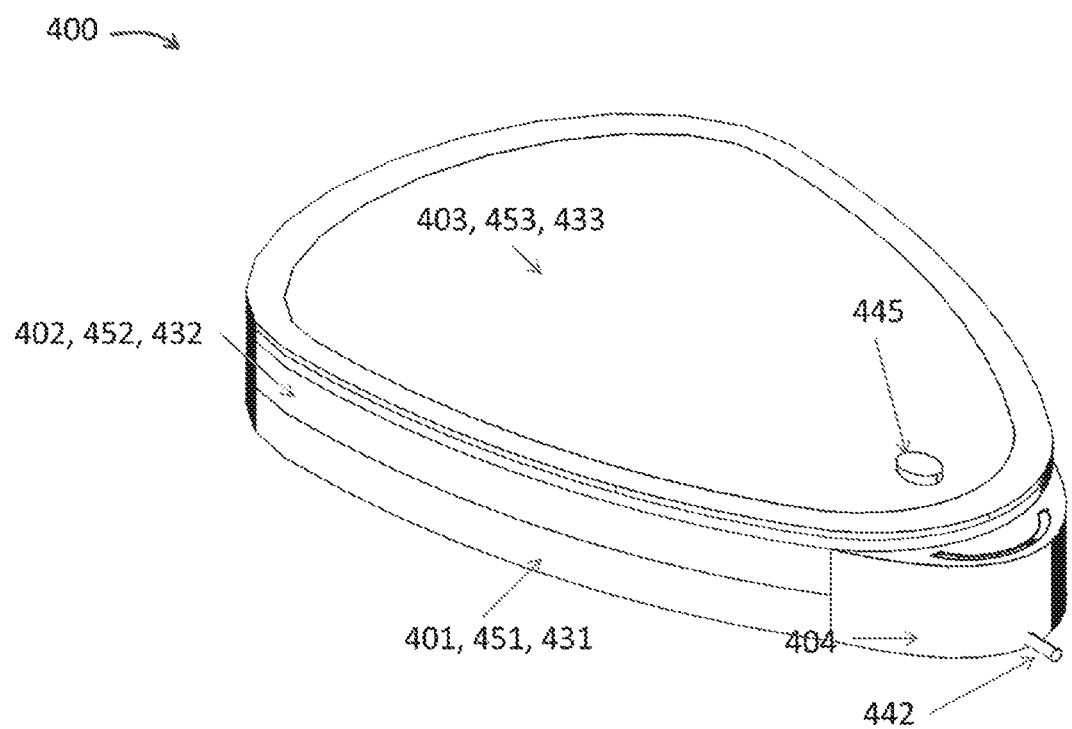
Figure 16B:
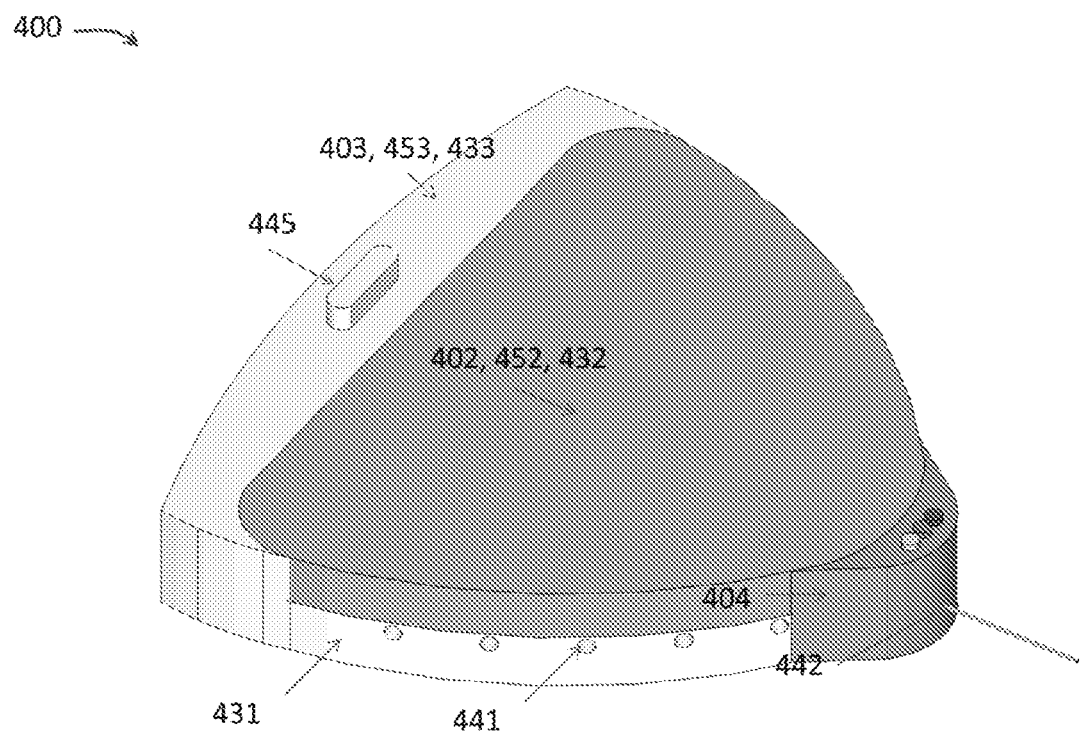

FIGS. 16a and 16b show different views of an embodiment.

FIGS. 17a, 17b, 17c and 17d show schematic views of different potential arrangements.

Figure 18:
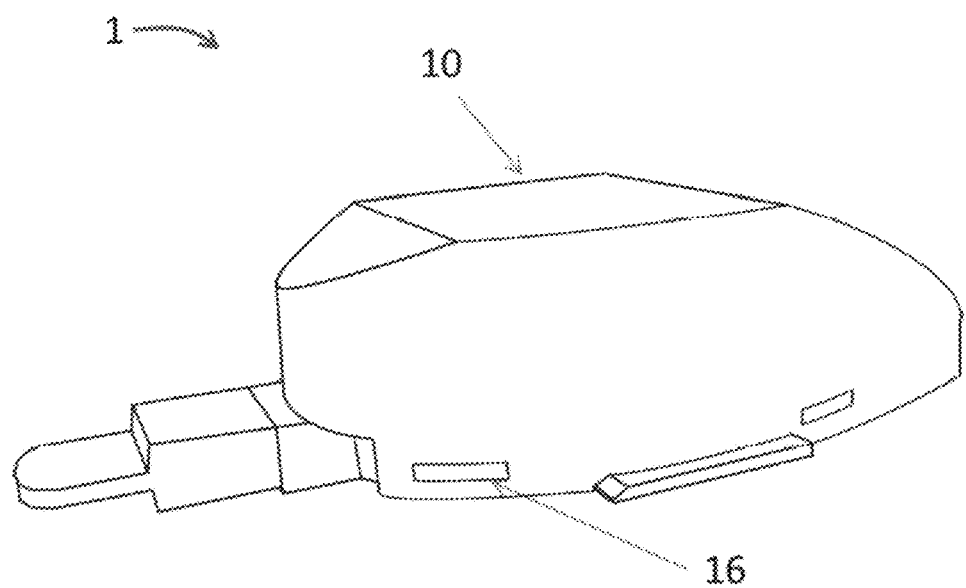

FIG. 18 shows a 3d view of a potential embodiment.

FIG. 19 shows several views of a potential filling indicator.

FIG. 20 shows several views of a potential infusion status indicator.

Figures 21A, 21B:
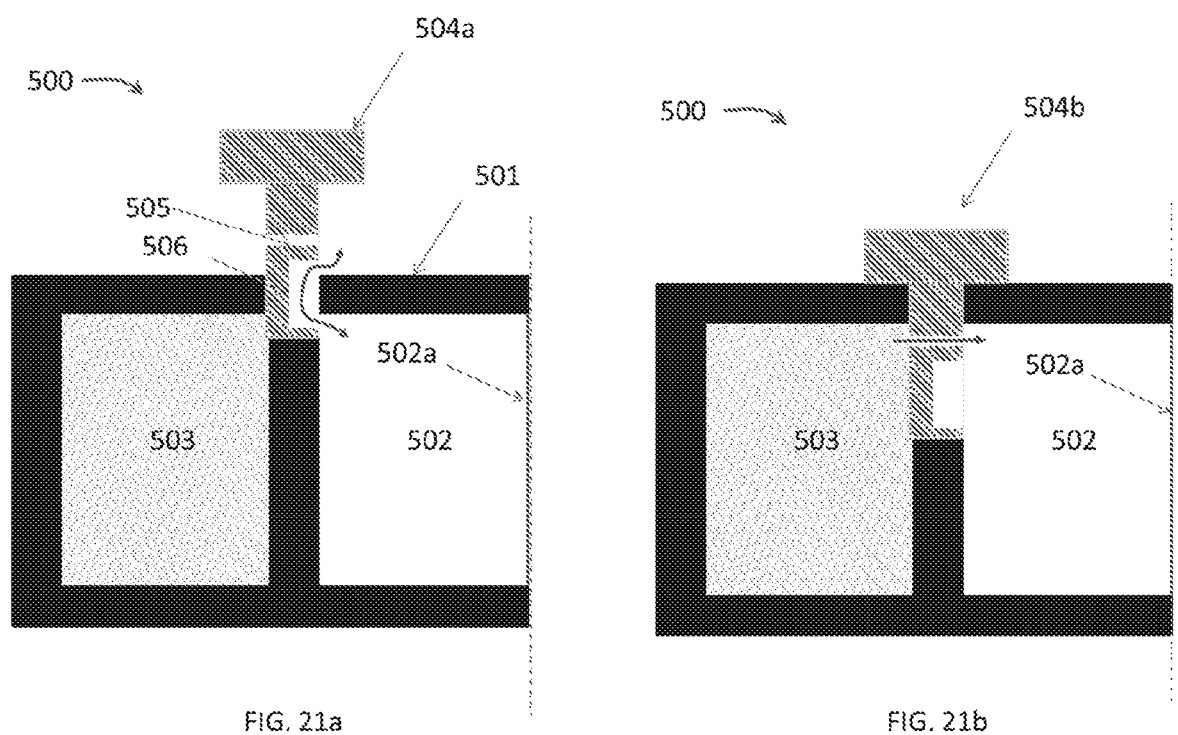

FIGS. 21a and 21b show different views of an embodiment comprising a vent device and a trigger device.

Figure 22A:
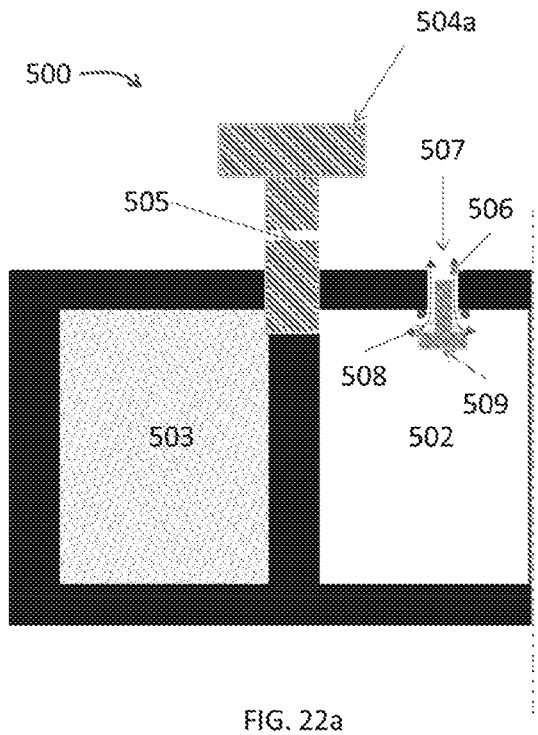
Figure 22B:
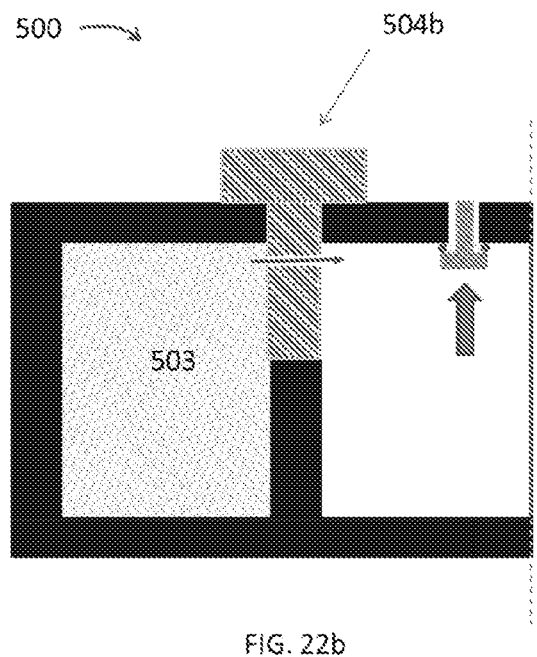

FIGS. 22a and 22b show different views of an embodiment comprising a vent device and a trigger device.

Figure 23A:
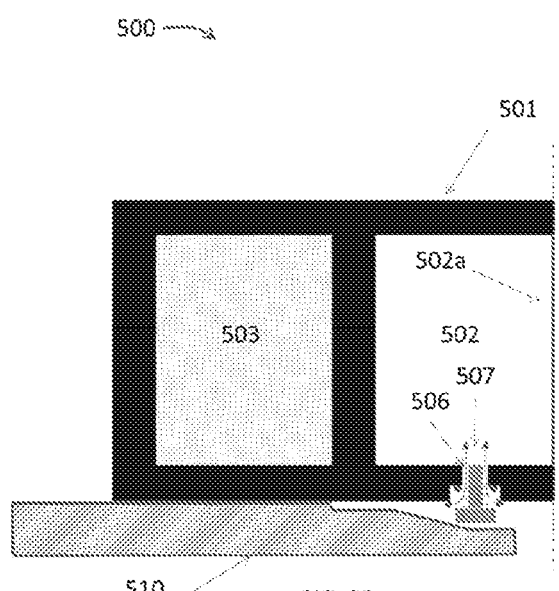
Figure 23B:
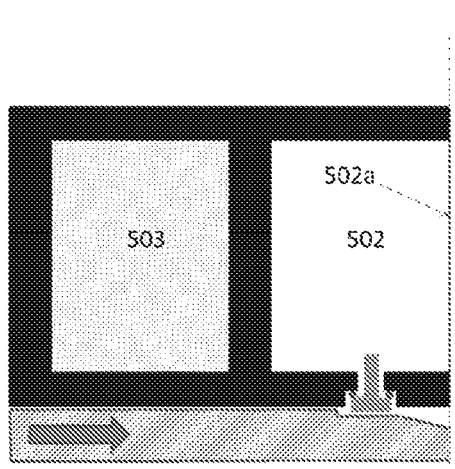

FIGS. 23a and 23b show different views of an embodiment comprising a vent device and a cradle unit.

FIGS. 24a, 24b, 24c, and 24d show schematic views of different status of an embodiment.

LIST OF ELEMENTS

1 Delivery system
2 Patient
3 Skin-adherable unit
4 Valve device/Fluid communication device
4a Valve device
4b Valve device/plug
5 Fluid channel
6 Containers' interface
6a First flexible membrane/movable wall
6b Second flexible membrane/movable wall
6c Third flexible membrane/movable wall
7 Injection device
8 Trigger device
9 Indicator
10 Housing
11 First container
11a Storage compartment of the first container
12 Second container
12a Storage compartment of the second container
13 Third container
13a Storage compartment of the third container
14 Pressurization device/means
15 Acting device/means
16 First venting element or vent device
16a Second venting element
17 Gap
18 Outlet port
19 Fluid pathway/Flow restrictor
20 Rigid part of the first container
21 Syringe
22 Inlet port
23 Concave internal structure of the first container
24 Concave internal structure of the second container
25 Rigid part of the second container
26 Valve device
27 Filter
28 Flexible sheet
29 Movement of collapse
30 Cavity
31 Channel
32 Outlet location
33 Length of the container
34 Width of the container
35 Rigid wall
36 First surface
37 Second surface
38 Proximal part
39 Distal part
40 Lower face
41 Upper face
42 View icon
43 Junction edge
44 Containers' interface cavity
45 First cavity
46 Second cavity
47 Filling indicator
48 Infusion status indicator
50 Container
51 Flexible wall
52 Opposite wall
53 First part
54 Second part
55 Outlet
100 Delivery system
101 First container
102 Second container
103 Third container
104 Indicator device
111 First storage compartment
112 Second storage compartment
113 Third storage compartment
121 First flexible membrane
122 Second flexible membrane
131 First housing
132 Second housing
140 Cavity
141 Vent
142 First fluid pathway
143 Second fluid pathway
145 Trigger device
200 Container
201 Flexible membrane
202 Rigid part of the first container
203 Rigid housing 204 Vent
205 Passage
206 Fluid pathway
207 Lid
208 Concave internal structure
209 External surface of the container
300 Container
301 Flexible membrane
302 Rigid part of the container
303 Fluid pathway
304 Edge of the flexible membrane
305 Support
306 Vent
307 External surface
308 Protrusion
400 Delivery system
401 First container
402 Second container
403 Third container
404 Indicator device
411 First storage compartment
412 Second storage compartment
413 Third storage compartment
421 First flexible membrane
422 Second flexible membrane
431 First rigid shell
432 Second rigid shell
433 Third rigid shell
440 Cavity
441 Vent
442 First fluid pathway
443 Second fluid pathway
445 Trigger device
446 Outlet
447 Inlet
451 Rigid part of the first container
452 Rigid part of the second container
453 Rigid part of the third container
500 Delivery system
501 Housing
502 Second container
502a Flexible membrane
503 Third container
504a Trigger device (button)—first position
504b Trigger device (button)—second position
505 Fluid pathway
506 Fluid pathway
507 Valve device
508 Spring
509 Moving body
510 Cradle Unit—Skin-adherable unit
600 Delivery system
601 First container
602 Second container
603 Third container
604 Medical device
605 Cradle unit
606 Movable wall
607 Transcutaneous device
608 Second venting element
609 First valve device
610 Trigger device
611 Second valve device
612 Patient skin
700 Delivery system
701 Filling indicator
702 First venting element
703 Valve device
704 Plunger
705 Plunger
706 Transparent cylinder

DETAILED DESCRIPTION OF THE DISCLOSURE

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, any direction referred to herein, such as "top", "bottom", "left", "right", "upper", "lower", and other directions or orientations are described herein for clarity in reference to the figures and are not intended to be limiting of an actual device or system. Devices and systems described herein may be used in a number of directions and orientations.

As used herein, "have", "having", "include", "including", "comprise", "comprising" or the like are used in their open ended sense, and generally mean "including, but not limited to.

As used in this specification and the appended claims, the term "or" is generally employed in its sense including "and/or" unless the content clearly dictates otherwise.

As used in this specification and the appended claims, "at least one of A, B, and C", "at least one of A, B or C", "selected from the group consisting of A, B, C, and combinations thereof" or the like are used in their open ended sense including "only A, or only B, or only C, or any combination of A, B and C" unless the content clearly dictates otherwise.

The present application claims the benefit of the priority of PCT/IB2019/051237 filed on 15 Feb. 2019, EP19155800.6 filed on 6 Feb. 2019, EP19151325.8 filed on 11 Jan. 2019, EP19151324.1 filed on 11 Jan. 2019, EP19151323.3 filed on 11 Jan. 2019, EP18157250.4 filed on 16 Feb. 2018, EP18182850.0 filed on 11 Jul. 2018 and of EP18215745.3 filed on 21 Dec. 2018 in the name of Debiotech SA, the entire disclosure of which are incorporated herein by reference.

1.1 General Concept

Figure 1:
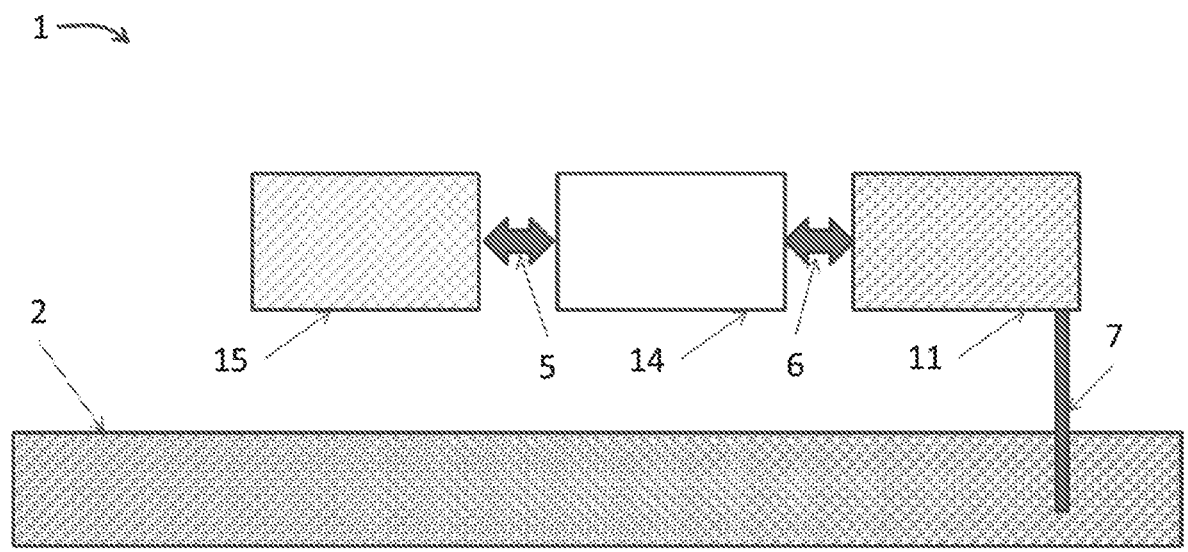
FIG. 1 shows a schematic view of the general concept according to an embodiment.

As shown by the FIG. 1, the delivery system (1) comprises a first container (11) adapted to store a medical fluid (such as a drug or a pharmaceutical fluid or other fluids). In this document, the medical fluid may be also called fluid or solution. The medical fluid may be a liquid or a gas, for example, an incompressible fluid, and is intended to be delivered to a patient (2) for example via a transcutaneous device (7). The transcutaneous device (7) may be in fluid communication with the first container (11) and may comprise for example a needle, a cannula, one or more micro needle or other means adapted or configured to bring the medical fluid to (into or on) the patient body.

The delivery system (1) further comprises a pressurization means (14) which may be operatively coupled (6) to the first container (11). For example, the pressurization means (14) may be adapted or configured to pressurize the first container so as to cause the flow of the medical fluid from the first container (11) to the patient (2). For example, if the first container (11) comprises a flexible membrane, the pressurization means (14) may be configured to act on the flexible membrane in order to pressurize the first container.

The delivery system (1) may further comprise an action means (15) which may be operatively coupled to the pressurization means (14). For example, the action means (15) may be adapted or configured to allow the pressurization of the first container preferentially via the pressurization means (14).

According to a preferred embodiment, the pressurization means (14) comprises a container (for example a second container (12)) and the action means (15) comprises a container (for example a third container (13)) in fluid communication or pressure communication with the pressurization means (14). The action means (15) may further comprise at least one of a valve device (4) and a fluid pathway (5) allowing fluid communication between the third container and the second container for example when the valve device (4) is in open position. At least one of the valve device and the fluid pathway may define a fluid communication device as described in this document. The third container may be configured or adapted to store a compressed fluid (in a compressed state) such as a propellant. The propellant may be a liquefied gas that exhibits a large value of vapor pressure at ambient temperature. The pressure range is therefore determined by the evolution of this vapor pressure within a predefined range of functioning temperature, typically from 5° C. to 40° C. Considering isobutane as a potential propellant, this pressure (absolute) is for instance 1.86 bar at 5° C., 3 bar at 20° C. and 5.25 bar at 40° C.

According to another embodiment, the pressurization means (14) may be a spring, an elastic device, an actuator which acts on the first container, a plunger, . . . And the actions means (15) may comprise an element adapted to generate a gas, such as a battery or other chemical elements, or to act on the pressurization means (14) . . .

The delivery system may be intended for single use. Thus, after a single use/delivery, the delivery system may be discarded, for example entirely discarded.

The delivery system (1) may be configured to deliver the entire volume of the solution stored in the first storage compartment in a single bolus. Thus, once the trigger device is activated, the delivery system will infuse the solution to the patient until the first storage compartment is substantially empty.

The delivery system may be adapted to inform the patient about the end of the delivery, via an indicator device (also called status indicator device).

In one embodiment, the delivery system may comprise an electronic device configured to control and/or monitor the delivery. Preferentially, the delivery system does not comprise any electronic element configured to convey the solution and/or to pressurize the first container and/or to control the pressurization means (14) and/or the action means (15). Nevertheless, an indicator device may comprise some electronic elements (embedded electronic device) such as a sensor (pressure sensor or other), a processor and/or a light indicator (LED, . . . ). The embedded electronic may be configured to send information to a tierce device. For example, the embedded electronic may comprise a communication device adapted to send data to a remote device (Smartphone, remote server, PC, PDA, . . . ). The embedded electronic may be configured to send information relative to at least one of a delivery state, a system status, treatment compliance, date and time of the treatment, infused volume, flow rate, end of the infusion, failure, anomaly, occlusion, leak, . . .

In one embodiment, the delivery system may be configured to operate without any electronic element and/or battery.

1.2 General Structure

The delivery system (1), disclosed by at least one of the FIGS. 2, 3, 4, 5, and 6, comprises at least one of:
  A first container (11)
  A second container (12), and
  A third container (13).

Preferentially, the first container (11) comprises a first storage compartment (11a), a first movable wall (for example a flexible wall/membrane) configured to change a capacity of the first container (11) (for example the volume of the storage compartment (11a)) and an outlet port allowing the solution to get out of the storage compartment (11a). The outlet port is configured to be in fluid communication with the transcutaneous device (7), for example when the delivery system delivers the solution to the patient.

Figure 6A:
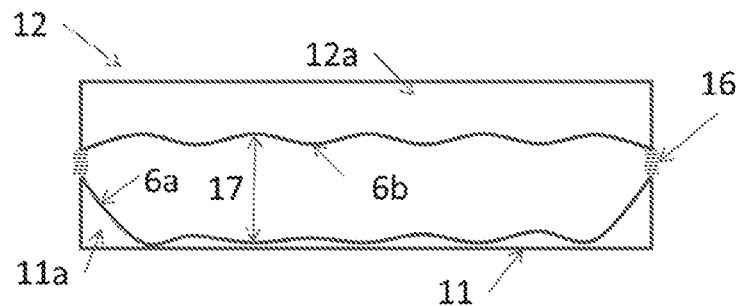
Figure 6B:
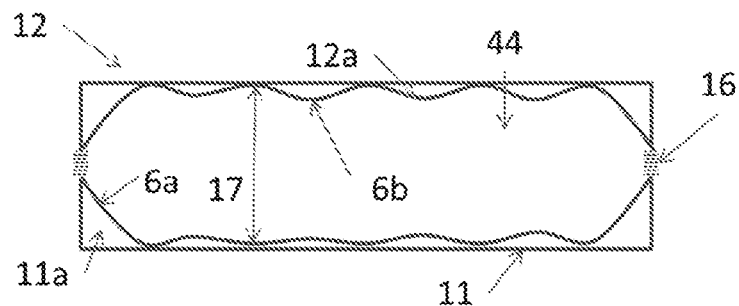
Figure 6C:
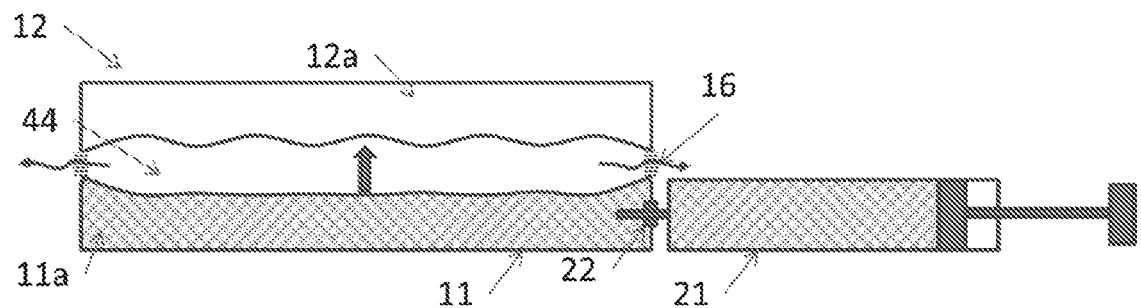

The first container may comprise an inlet port to fill the storage compartment (11a) with the solution intended to be delivery to the patient (as shown by FIG. 6c). The inlet port and the outlet port may be the same port or the inlet port may be a different port from the outlet port.

As shown by the FIG. 8, the delivery system (1) may further comprise a flow restrictor (19) arranged between the outlet port (18) of the first container (11) and the transcutaneous device (7). The flow restrictor (19) may be configured to regulate the flow of solution delivered to the patient when the solution stored in the first container is submitted to a determined range of pressure. For example, the target flow rate may be comprised between 0 and 10 ml/min, preferentially between 0.01 and 5 ml/min and more preferentially between 0.05 and 3 ml/min. The flow restrictor (19) may comprise a fluid pathway configured to provide a predetermined fluid resistance between the first reservoir and the patient. The flow restrictor (19) may be configured in order to provide the main fluid resistance from the first storage compartment to an end of the transcutaneous device. The flow restrictor (19) may be arranged into or secured to at least a rigid part (20) of the first container. The flow restrictor (19) may be composed of at least one part.

The fluid pathway is preferentially straight but it may comprise one or several curved sections.

The fluid pathway may comprise a hollow rod which may be made from at least one of the following materials: metal, plastic, silicon, ceramic or glass. The hollow rod may comprise a sharp end (such as a needle) configured to be inserted into the transcutaneous device.

Other examples of flow restrictor (which may be implemented in the delivery system) have been described by at least one of the following documents: WO2010020891A1, WO2011098946A1, WO2014108860A1, and WO2011098867A1. The contents of these documents are incorporated by reference in the present document.

The pressure means (14) (for example the second container and the propellant) and the flow restrictor (19) may be configured in order to reach a substantially constant flow rate for substantially the entire duration of the infusion.

The delivery system may comprise a valve device (26) (as shown by the FIG. 2) arranged between the first storage compartment and the transcutaneous device and configured to control the fluid communication between the first storage compartment and the patient. This valve device may comprise a first position/state/condition in which the valve prevents the flow of the solution to the patient and a second position/state/condition in which the valve allow the solution to flow to the patient. The valve may be a mechanical valve (e.g. mitral valve, duckbill valve . . . ) or a capillary valve (e.g. a hydrophobic membrane . . . ). For example, a hydrophobic membrane may be configured to prevent the flow of liquid as long as the pressure in the liquid is not large enough to overcome this capillary barrier. This latter solution may be interesting because the reservoir remains vented after final assembly. This pressure equilibration may be required by the sterilization or the final packaging process.

Preferentially, the second container (12) comprises a second storage compartment (12a), a second movable wall (for example a flexible wall/membrane) configured to change capacity of the second container (12) (for example the volume of the second storage compartment (12a)). More particularly, a change of the volume of the second storage compartment induces a movement of the second movable wall (for example a movement/deformation/stretching of the flexible membrane). The second container may comprise an inlet port. The second container (12) may comprise an outlet port (which may be a vent device as described thereafter) configured to expel the propellant from the second container for example at the end of the delivery.

Preferentially, the first container (11) and the second container (12) comprise a containers' interface (6) configured in such a manner that the first container and the second container are in pressure communication when the first movable wall and the second movable wall are at least partially in contact.

As disclosed by the FIG. 6, the containers' interface (6) may comprise a cavity defined by at least a first surface (6a) of the first movable wall and a second surface (6b) of the second movable wall. Preferentially, the first surface (6a) is arranged opposite to the second surface (6b). The containers interface (6) may be configured in such manner that the first surface (6a) may be:
- spaced apart from the second surface (6b), when the delivery system (1) is in a first state (for example an initial state of the delivery system), and/or
- in contact with the second surface (6b) when the delivery system (1) is in a second state (for example a delivery state of the delivery system or following the activation of the infusion).

The cavity of the containers' interface may have a variable volume depending on the delivery state. This cavity is preferentially vented by a vent device as described below.

The vent device may comprise a first venting element (16) (for example an aperture) intended to allow fluid communication between at least an inside part of the delivery system and the outside environment of the delivery system. The first venting element may be configured to keep the cavity of the containers' interface (6) vented.

In some embodiments, the first venting element may be configured to provide a pressure equilibration of the containers' interface cavity to the (external ambient) atmosphere (for example with the (external) air surrounding the delivery system which may be at the atmospheric pressure), preferentially when at least one of the first storage compartment volume and the second storage compartment volume varies.

In some embodiments (for example shown by FIGS. 2 and 19), the first venting element may comprise an occlusion device (4b, 703) such as a valve device or a plug. The occlusion device may be configured to open or close the first venting element at appropriate time(s). For example as described thereafter, during the filling of the first container, in order to use a filling indicator, the occlusion device may close the first venting element. Thus as the solution is injected into the first storage compartment, the first venting element cannot expel the air outside and causes a pressure increase transmit to the filling indicator or to a pressure transducer such as a pressure sensor (if the filling indicator is operatively coupled with a pressure transducer). After the filling, the occlusion device may be removed (or disable) in order to open the first venting element (so as to render the first venting element operable) and to expel air trapped into the containers' interface cavity.

In some embodiments, the first venting element may be configured to expel (outside the delivery system) the air/fluid (trapped) present into the containers' interface cavity when the first movable wall moves towards the second movable wall and/or when the second movable wall moves towards the first movable wall.

In some embodiments, the first venting element may be configured to allow air/fluid entry into the containers' interface cavity when the first movable wall moves away from the second movable wall and/or when the second movable wall moves away from the first movable wall.

In some embodiments, the first venting element may comprise one or more aperture (for example a through hole). The vent device may further comprise a hydrophobic membrane, a filter or a coating configured to prevent the flow of water into the enclosure. The first venting element may comprise a baffle configured to prevent the insertion of a straight and rigid tip through the venting element.

An example of a vent device which may be comprised in the delivery system is described by the United States Patent: U.S. Pat. No. 9,872,955, the entire disclosure of which is incorporated herein by reference.

In some embodiments, the second container may comprise a second venting element (16a) (as shown by the FIGS. 2 and 3a) providing an air/fluid communication of the second storage compartment (12a) with an outside environment of the delivery system. For example, such second venting element may provide a pressure equilibration of the second storage compartment to the (external ambient) atmosphere (for example with the (external) air surrounding the delivery system which may be at the atmospheric pressure) for example during a storage time period or during the filling process of the first storage compartment or to discharge the pressure of the second storage compartment after the delivery.

In case of a (unintended) leakage of the third storage compartment into the second storage compartment, the second venting element (16a) may prevent any unintended pressure increase into the second storage compartment (12a).

During the storage time period, the delivery system may be stored in a cavity of a closed (e.g. sealed) packaging. In this case (and until the packaging is open) the second venting element may provide an air/fluid communication of the second storage compartment (12a) with the cavity of the packaging.

During the filling of the first storage compartment, if the second storage compartment is not empty, the first movable wall may exert a force (due to the volume increase during the filling process) on the second movable wall and may decrease the volume of the second storage compartment. In this case, for example, the second venting element may prevent any (unintended) pressure increase and/or may make the filling process easier and more efficient.

At the end of the infusion (after solution delivery), the second venting element may discharge the pressure present in the second storage compartment. Thus, the delivery system may be discarded without or with a limited pressure in at least one of the first, second and third storage compartment.

The second venting element (16a) may be configured to be enabled and/or disabled, for example, the second venting element may comprise a valve device (4a) having two positions:
- a first position providing an air/fluid communication of the second storage compartment (12a) with an outside environment of the delivery system and
- a second position preventing any (unintended) air/fluid communication of the second storage compartment (12a) with an outside environment of the delivery system.

The second venting element (16a) may comprise a (slight) controlled leak, for example, one or more small hole(s) and/or a porous material, configured to provide an air/fluid communication with determined fluid resistance. The controlled leak may be configured to ensure that the solution is wholly infused to the patient (after activation of the delivery system) and to allow the pressure to be slightly expelled to the outside (at least after the solution delivery). Thus, the controlled leak is designed in such a manner that the second container comprises or keeps enough propellant (gas at a minimal pressure) to exert a determined pressure to the first container during the whole duration of the infusion.

The porous material and/or the small hole may be arranged on at least a part of the wall of the second container such that a (slight) controlled leak may occur. For example, the second movable wall may comprise a silicone material or other porous material.

In some embodiments, the second venting element may comprise one or more aperture (for example a through hole). As described above, the vent device may further comprise a hydrophobic membrane, a filter or a coating configured to prevent the flow of water into the enclosure. The second venting element may comprise a baffle configured to prevent the insertion of a straight and rigid tip through the venting element.

The FIGS. 21a and 21b show a part of an embodiment of a delivery system (500) which comprises a housing (501) in which is arranged a first container (not shown), a second container (502) and a third container (503). The third container (503) comprises rigid walls configured to keep the gas (propellant) in a compressed state. The second container is configured to receive the gas from the third container when the delivery system has been activated. The second container comprises a flexible membrane (502a) configured to exert pressure on the first container when the delivery system is activated. The delivery system further comprises a trigger device (504). The trigger device (504) comprises a first position (504a—FIG. 21a) and a second position (504b—FIG. 21b). The trigger device (504) may comprise at least one fluid pathway (505, 506). As a valve device (4, 4a) described above, the trigger device (504) may be configured in order to:
- provide fluid communication between the second container and the outside of the delivery system via the at least one fluid pathway (505, 506) and to prevent fluid communication between the second container and the third container, when the trigger device is in the first position; and/or
- provide fluid communication between the second container and the third container via the at least one fluid pathway (505, 506) and, preferentially, to prevent fluid communication between the second container and the outside of the delivery system, when the trigger device is in the second position.

The FIGS. 21a and b show a trigger device (504) comprising two distinct fluid pathways nevertheless all or part of these fluid pathways (505, 506) may comprise common section.

A small (slightly) controlled leak may be designed to decrease the pressure after activation and/or, the user may be prompted to act on (e.g. pull) the trigger device (504) to open the fluid pathway (506) at the end of the infusion.

The FIGS. 22a and 22b show a part of another embodiment of a delivery system (500). Here the delivery system comprises a valve device (507) having a moving body (509) configured to open and close a fluid pathway (506). The valve device (507) may be configured in order to:
- provide fluid communication between the second container and the outside of the delivery system via the fluid pathway (506), when the valve device (507) is in the first position; and/or
- prevent fluid communication between the second container and the outside of the delivery system, when the valve device (507) is in the second position.

The valve device may comprise an elastic device (for example a spring (508)) configured to maintain the valve device in a predetermined position.

For example, the elastic device may maintain the valve device in a second position (closed) and action may be required to open the valve (for example before or during the first container filling or before the activation of the infusion or after the delivery). For example, the user may be prompted to push on the valve device (e.g. the moving body) to open the valve device (507).

The FIG. 22a shows a valve device (507) in a first position (open) and the spring maintains the valve device in this position. The valve device may be designed in such a manner that the moving body is maintained open until a predetermined pressure is reached in the second container. Thus when the pressure in the second container reaches a predetermined pressure, the moving body is moved by the pressure and closes the fluid pathway as illustrated by FIG. 22b. A slightly controlled leak may be designed to decrease the pressure after activation and/or, the user may be prompted to push on the moving body to open the valve device at the end of the infusion.

The FIGS. 23a and 23b show a part of another embodiment of a delivery system (500). Here, the delivery system comprises a valve device (507) having a fluid pathway (506) and a cradle unit (510) configured to fix the delivery system to the patient skin. The valve device and the cradle unit may be configured to be operatively coupled such that the fluid pathway is open or closed depending on the relative position of the cradle unit and the valve device.

For example, FIGS. 23a and b show two relative positions:
- a first relative position, wherein the fluid pathway (506) is not occluded (FIG. 23a), which may provide fluid communication between the second container and the outside of the delivery system via the fluid pathway (506), and a second relative position, wherein the fluid partway is occluded (FIG. 23b), which may prevent fluid communication between the second container and the outside of the delivery system.

Preferentially, the second relative position is required the whole duration of the infusion.

In some embodiments, the cradle unit is configured to occlude the fluid pathway when there are in the second relative position.

In some embodiments, the delivery system may comprise a valve device (507) having a moving body (509) configured to open and close a fluid pathway (506) in collaboration with the cradle unit. The valve device may further comprise an elastic device (for example a spring) configured to maintain the valve device in a predetermined position.

In some embodiments, a trigger device (as disclosed above) may be adapted to be also operatively coupled with a cradle unit. Furthermore, the trigger device (504) shown in FIG. 21 may be arranged in order to be operatively coupled with the cradle unit as described above.

Preferentially, as described above (FIG. 2), the third container (13) comprises a third storage compartment (13a) configured to store a compressed fluid (in a compressed state) such as a propellant. The third container may comprise rigid walls in such a manner the volume of the third storage compartment (13a) is constant. The volume of the third storage compartment is preferentially the same when it is empty or filled with propellant (in a compressed state). The third container comprises an outlet port configured to be in fluid communication with the second storage compartment in a delivery state in such a manner that the compressed fluid flows from the third storage compartment to the second storage compartment.

The delivery system may comprise a valve device (4) (also called fluid communication device) configured to prevent the fluid communication (or to isolate the second storage compartment from the third storage compartment) when the valve device is in a first state/position (for example closed) and to allow the fluid communication between the second storage compartment and the third storage compartment when the valve device in a second state/position (for example open).

The delivery system may comprise a trigger device (8). The trigger device may be configured to initiate a change of delivery system state. Preferentially the trigger device is operatively coupled to the valve device (4) (for example mechanically). The trigger device may be configured to change the state/position of the valve device (4) in order to pass from a first state (first position) to a second state (second position) and/or vice versa.

The trigger device (8) may comprise a button such as a push or a sliding button, a timer, and/or a countdown mechanism. When the trigger device is activated (for example by the user/patient), the trigger device is configured to initiate the change of the delivery system state or to launch the countdown or the timer.

The delivery system may comprise a status indicator (9) as disclosed by the European patent application number EP18157250.4 or international patent application PCT/IB2019/051237, the entire disclosure of which are incorporated herein by reference. The indicator device may be operatively coupled to at least one of the first container, the second container, the third container, and the transcutaneous device. The indicator device (9) may be configured to provide information to the user concerning the status of the delivery system or one of the listed elements, for example: Occlusion, ready, ready to be activated, ready for filling, ready to infuse, delivery in progress, error, full storage compartment, empty storage compartment, delivery finished, . . .

The delivery system may comprise one or several parts. As disclosed by FIG. 2, the delivery system may be a single block device. In this case, the delivery system (1) comprises at least one housing (10) in which the first, the second and the third containers are arranged. These three containers may not be separated or removed from the housing (10).

Figure 4A:
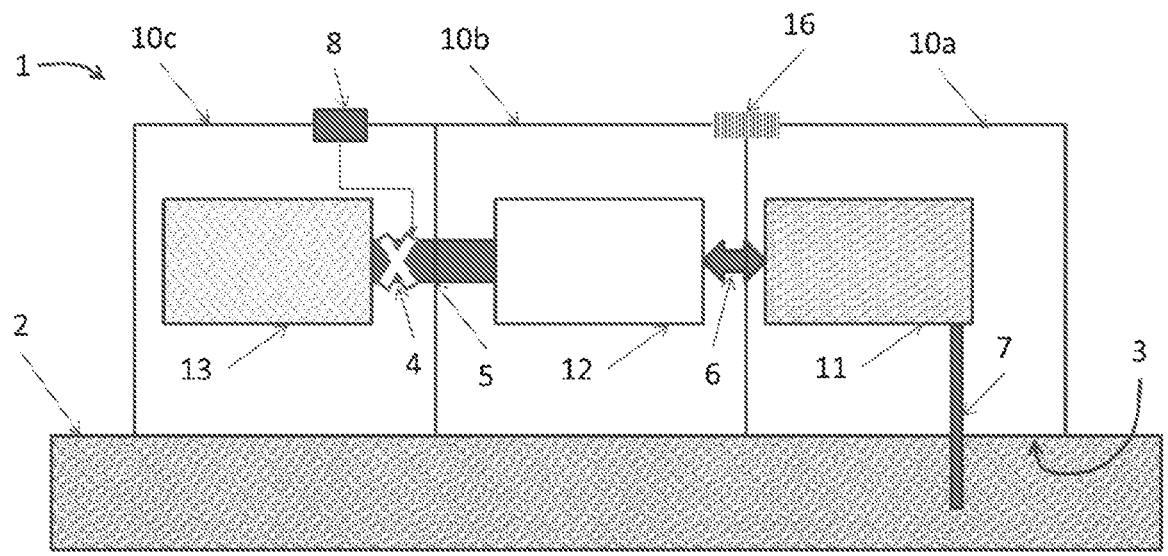
Figure 4B:
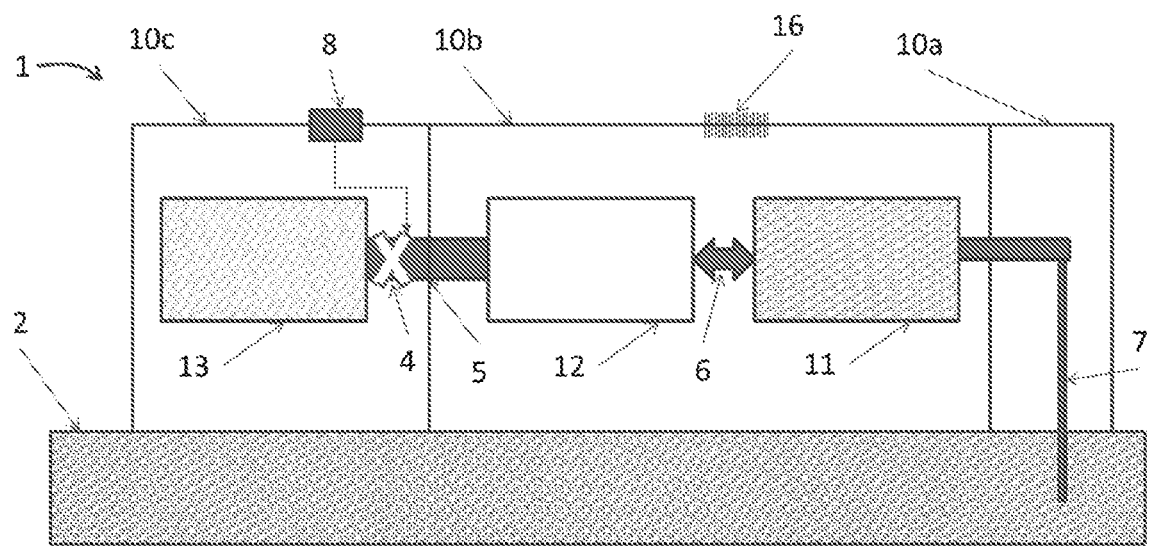
Figure 4C:
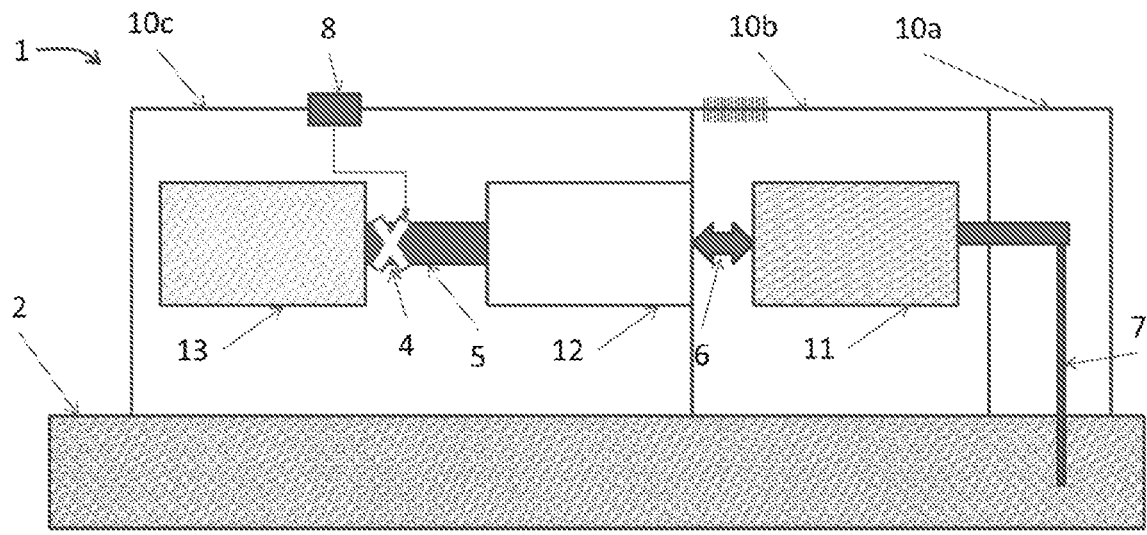
Figure 4D:
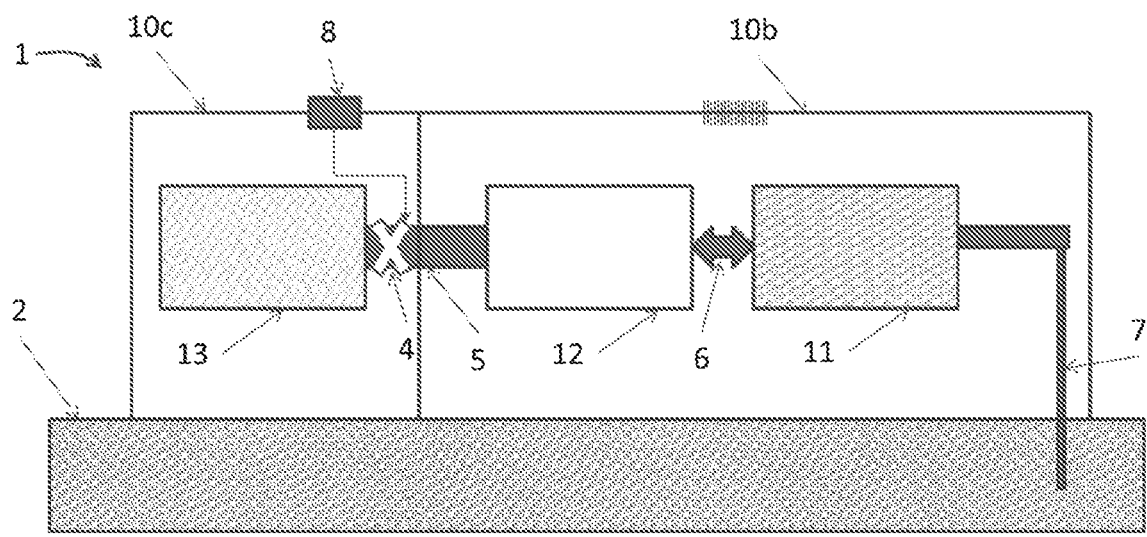

As disclosed by the FIGS. 4a, b, and c, the delivery system may be modular and/or may comprise several parts. A first part may comprise a first housing (10a) in which at least one of the first storage container and at least a part of the transcutaneous device may be arranged. A second part may comprise a second housing (10b) in which at least one of the first storage container, the second storage container and at least a part of the transcutaneous device may be arranged. A third part may comprise a third housing (10c) in which at least one of the first storage container, the second storage container, the third storage container and at least a part of the transcutaneous device may be arranged.

The vent device may be arranged on at least one of the first, the second and the third housing, preferentially in fluid communication with the containers' interface (6).

The housings or the containers may be configured to be coupled there between in order to form the delivery system. The coupling process may be performed during the manufacturing process or by a user before the use.

The housing may comprise rectangular shape, trapezoidal shape, egg shape, butterfly shape, disks shape, triangular shape or ellipsoidal shape. Preferentially the housing is thin with smooth angles.

Preferentially, to solve problems related to the recycling of waste, at least one of the second container and the third container may be configured to be removable from the first container, for example at the end of the treatment. Thus at least one of the containers may be discarded in appropriate waste.

At least one of the third container and the second container may be adapted to the compressed fluid (propellant) and/or to the physical features (volume, viscosity, . . . ) of the solution stored in the first container. In other terms, the features (shape, dimension, material, . . . ) of the third container and/or the second container are designed by taking into account the physical features (volume, viscosity, . . . ) of the compressed fluid (propellant) and/or the physical features (volume, viscosity, . . . ) of the solution stored in the first container.

The delivery system may comprise a skin-adherable unit (3) configured to secure the delivery system to the patient skin. The skin-adherable unit may comprise a first side having an adhesive surface facing toward the skin surface of the patient for adhesion and a removable cover for covering the skin-adherable unit. The skin-adherable unit may further comprise a frame and coupling device configured to (optionally removably) secure the delivery system.

1.3 Containers' Interface

Figure 5A:
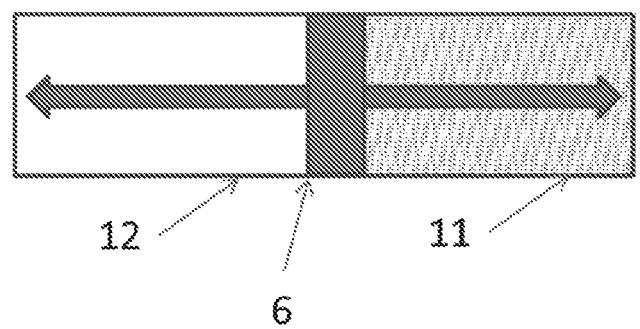

The FIGS. 5a, b, c, d, e, f and g contain non-limiting examples of the containers' interface (6).

In the FIG. 5a, the containers' interface (6) is at least one plunger delimitating the capacity of the first and the second containers. When the second container (12) is pressurized by a fluid, the plunger is moved causing the flow of solution of the first container (11). In this example, the first and second containers further comprise rigid walls and the plunger slides against the rigid walls.

Figure 5B:
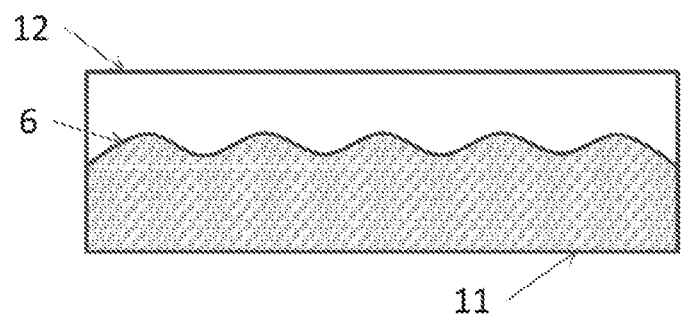

In FIG. 5b, the containers' interface (6) comprises a single flexible membrane wherein the first movable wall and the second movable wall are formed by the single flexible membrane. In this example, the first and/or second containers may further comprise rigid walls. And the single flexible membrane may be configured to move away and/or from the rigid wall of first and/or second containers.

Figure 5C:
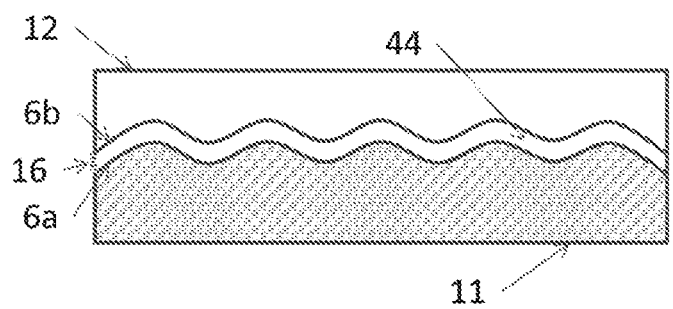

In FIG. 5c, the containers' interface (6) comprises two distinct flexible membranes. The first movable wall of the first container (11) comprises a first flexible membrane (6a). The second movable wall of the second container (12) comprises a second flexible membrane (6b). The first and/or second containers may further comprise rigid walls. The first flexible membrane may be configured to move away from and/or toward the second container (12). The second flexible membrane may be configured to move away from and/or toward the first container (11). The containers' interface (6) may comprise a containers' interface cavity (44). This containers' interface cavity (44) is arranged into the delivery system (for example into a housing). Preferentially, the containers' interface cavity (44) is at least partially defined by the first flexible membrane (6a) and the second flexible membrane (6b). This cavity may be vented by a vent device (16) for pressure equilibration when the volume of at least one of the first container (11), the second container or the enclosure varies or when at least one of the first flexible membrane and the second flexible membrane moves.

Figure 5D:
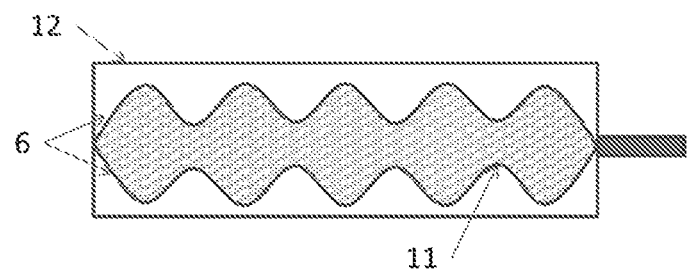

In FIG. 5d, the container's interface (6) comprises at least one flexible membrane wherein the first container is a flexible container. In this case, the first container (11) may be arranged into the second container (12).

Figure 5E:
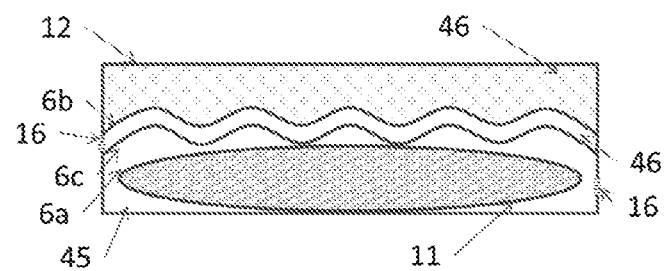
Figure 5F:
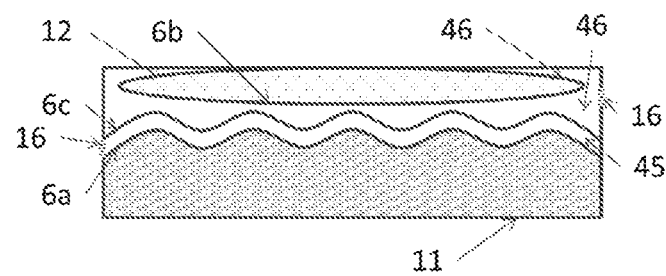
Figure 5G:
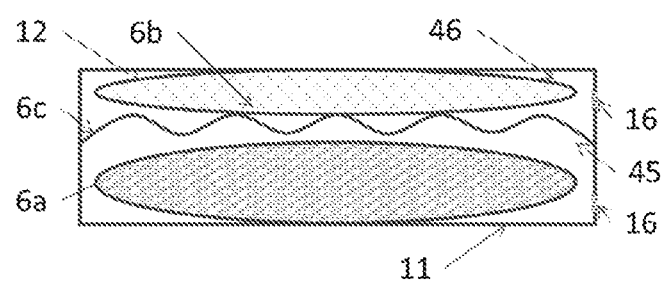

According to the FIGS. 5e, 5f, and 5g, the containers' interface (6) comprises two distinct flexible membranes. The first movable wall of the first container (11) comprises a first flexible membrane (6a). The second movable wall of the second container (12) comprises a second flexible membrane (6b). The first and/or second containers may further comprise rigid walls or may be a flexible pouch (such as a balloon). The first flexible membrane may be configured to move away from and/or toward the second container (12). The second flexible membrane may be configured to move away from and/or toward the first container (11). The containers' interface (6) may further comprise at least one cavity (45, 46) arranged into the delivery system (for example into a housing).

A first cavity (45) may be defined by at least one of a third flexible membrane (6c) and the first flexible membrane (6a). The third flexible membrane (6c) may be configured to move away from and/or toward the first container (11) (or the second container (12)) and to vary the volume of the first cavity (45). The first cavity may comprise a dedicated vent device (16) configured to vent the first cavity for pressure equilibration for example when the first container (11) is being filled.

A second cavity (46) may be defined by at least one of a third flexible membrane (6c) and the second flexible membrane (6b). The third flexible membrane (6c) configured to move away from and/or toward the first container (11) (or the second container (12)) and to vary the volume of the second cavity (46). The second cavity may comprise a dedicated vent device (16) configured to vent the second cavity for pressure equilibration for example when at least one of the second flexible membrane (6b) and the third flexible membrane (6c) moves or when the volume of at least one of the first storage compartment and the second storage compartment varies.

The third flexible membrane may be configured to provide additional insulation (shock and/or thermal) to the first container (11). Furthermore, in the case of second container leakage, the fluid initially stored in the second storage compartment may exit by the dedicated vent device (16).

According to the FIGS. 5e and 5g, the first container is arranged into the first cavity (45).

According to the FIGS. 5f and 5g, the second container is arranged into the second cavity (46).

1.4 Delivery System States

The FIG. 6 show different potential states of the delivery system, in particular, the first and the second container.

Figure 12A:
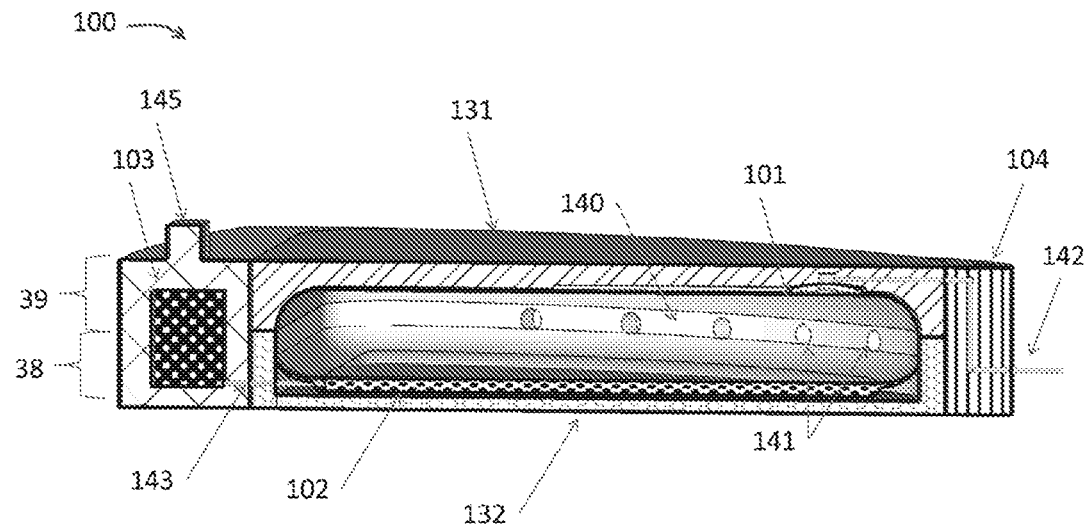
Figure 12B:
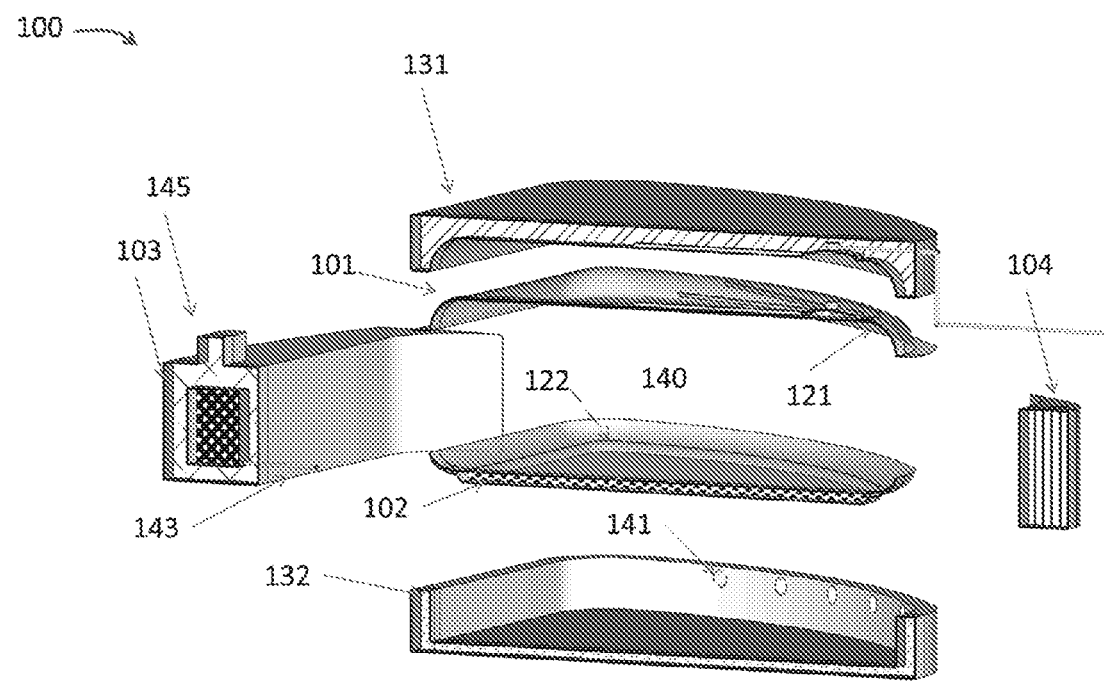

Initial State:

In one embodiment, as disclosed by the FIGS. 6a and b, the first storage compartment does not initially store the solution (for example before the delivery, when the delivery system is in the packaging). Preferentially, the volume of the first storage compartment is initially minimal. In this case, the first storage compartment is initially substantially empty. The movable wall may be in contact (or very close to or in the closest manner) with the opposite internal wall of the first container (for example on a substantial length of the first storage compartment), for example against the internal wall of the rigid part (20) of the first container (11). The FIG. 12a shows an example of an embodiment in initial sate comprising a first storage compartment which is substantially empty.

In another embodiment (for example as the state of the system shown by FIG. 6d), the first storage compartment initially stores the solution. In this case, the volume of the first storage compartment may be maximal.

In both cases, preferentially, the movable walls of the first and the second containers are not in contact in order to not exert any non-intentional pressure to the first container. Furthermore, as disclosed above, the containers' interface may be vented by first venting element (16).

At the initial state of the delivery system, the gap (17) between the first surface (6a) of the first movable wall and a second surface (6b) of the second movable wall may be maximal and/or the volume of the containers' interface cavity (44) may be maximal.

Preferentially, the volume of the second storage compartment is initially minimal. Nevertheless, the second storage compartment may be non-empty and initially store a fluid such as a gas (for example air trapped during the manufacturing process).

As the third container (not shown by FIG. 6) preferentially comprises only rigid walls, the volume of the third storage compartment is constant. And, the third storage compartment may or may not initially store the compressed fluid.

Filling Step:

If the first storage compartment does not initially store the solution, the user has to fill the first storage compartment before use and the first container may comprise an inlet port (22) configured to fill the first storage compartment with the solution.

The FIG. 6c shows the filling of the first container via a syringe (22), the volume of the first storage compartment increases and the volume of the containers' interface cavity decreases. The first surface (6a) of the first movable wall moves toward the second container, for example toward the second surface (6d) of the second movable wall. The fluid (for example the gas trapped into the containers' interface cavity) may be discharged/expelled to the outside of the delivery system through the first venting element (16).

As disclosed by the FIG. 8, the second container may comprise a concave internal structure (24) which may be rigid. The second movable wall may be configured to closely match the concave internal structure (24). During the filling step, the first movable wall may move at least partially into the concave internal structure of the second container.

If the third storage compartment does not initially store the compressed fluid, the user has to fill the third storage compartment before use and the third container may comprise an inlet port configured to fill the third storage compartment with the compressed fluid.

In order to monitor the volume injected during the filling, the delivery system may comprise a filling indicator. The filling indicator may display the volume injected as the solution is injected into the first container and/or may indicate the end of the filling (filling volume reached). The filling indicator may be operable coupled to the first container. For example, the filling indicator may be is pressure communication with the first container. In this case, the filling indicator may comprise a pressure transducer and the first venting element may be occluded during the filling such that, as the first variable volume increases, the pressure increases and the filling indicator converts this pressure increase in a visual, tactile or sonor indication for the user.

Full Drug State:

At the end of the filling step, the gap between the first surface (6a) of the first movable wall and a second surface (6b) of the second movable wall is substantially reduced. The first surface (6a) of the first movable wall and a second surface (6b) of the second movable wall may or may not be in contact. The pressure exerted on the first movable wall, if any, must be limited and not induce a flow of the solution to the patient.

Figure 6D:
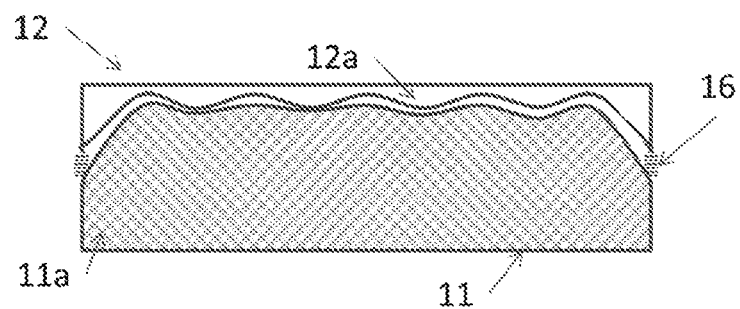
Figure 6E:
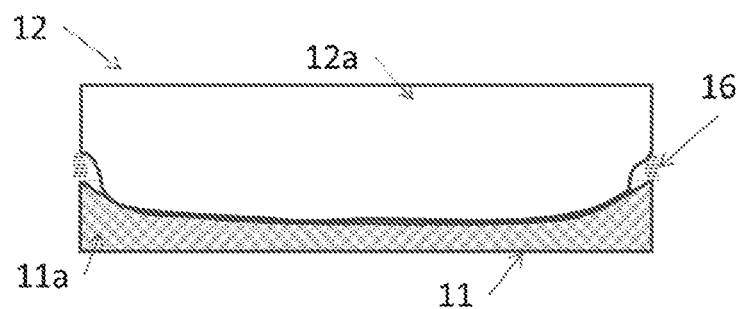

As disclosed by FIG. 6d, when the first storage compartment is full, the first movable wall may be at least partially deployed into the concave internal structure (24).

At this state, the indicator device (not shown) may indicate that the delivery system is ready to infuse or the drug container is full.

Activated/Delivery State:

After the trigger device has been activated (for example as soon as or after a predetermined time period), the trigger device initiates a change of the delivery system state. The valve device (4) switches from a first state/position (closed position) to a second state/position (open position). A second state/position of the valve device induces a flow of the compressed fluid from the third storage compartment to the second storage compartment. The second movable wall moves toward the first container due to the fluid pressure of the compressed fluid. The fluid pressure of the compressed fluid into the second container induces a displacement (a bending) of the second movable wall which exerts a pressure on the first movable wall.

At least during the delivery, the second movable wall is configured to come into contact with the first movable wall on at least 50, preferentially at least 80%, more preferentially at least 90% for example (substantially) on 100% of the first movable wall surface.

The fluid pressure of the second container is transmitted (at least partially or substantially) to the first container, in particular to the solution stored in the first storage compartment. Furthermore, the pressure causes a flow of the solution to the transcutaneous device.

The volume of the second storage container and/or the quantity of compressed fluid are adapted in order to have a substantially constant fluid pressure during a predetermined time period of the delivery. For example this predetermined time period may be at least 50% of the time period necessary to substantially drain the first storage compartment, preferentially at least 80%, more preferentially at least 90%, for example at least equal to the time period necessary to substantially drain the first storage compartment. In the latter case, the fluid pressure is constant over the entire duration of the delivery.

1.5 Containers Features

As disclosed above (FIG. 2), the first container (11) may comprise a first movable wall configured to change a capacity of the first container (11) (for example the storage compartment (11a)) and an outlet port configured to be in fluid communication with the transcutaneous device (7). The first movable wall may comprise/be a flexible membrane. The first container may comprise two flexible membranes sealed together. The first container may further comprise a rigid part. The rigid part may comprise at least the outlet port and/or an inlet port configured to fill the storage compartment (11a). The internal walls of the rigid part and of the flexible membrane may define the first storage container.

The storage compartment may be configured to receive and to store a volume of the solution comprised between 0 and 100 ml, preferentially between 1 and 10 ml for example 5 ml. The viscosity of the solution may be comprised between 0 and 100 cP, preferentially between 1 and 80 cP, more preferentially between 10 and 65 cP at 20° C., for example, 25 cP.

One of the inlet port and the outlet port of the first container may be covered by a filter (27) such as a hydrophilic filter configured to allow the passage of liquid and prevent the passage of gas (for example air).

The outlet port may be covered by a hydrophobic filter configured to prevent the flow of the solution outside of the first storage compartment until the pressure of the solution reaches a predetermined threshold. The hydrophobic filter may be used here as a valve device in order to infuse the solution only when a predetermined pressure is reached into the first and/or the second storage compartment (or a predetermined differential pressure between the pressure in the first storage compartment and the outlet port (downstream the filter)). The hydrophobic filter may be characterized by a threshold pressure that is typically at least 2 times larger than the maximum drug reservoir filling pressure (typically few tenths of mbar due to the reservoir film unfolding) and at least 2 times smaller than the minimum infusion pressure (e.g. the vapour pressure of the propellant at 5° C.)

Preferentially, the first container (11) comprises a rigid part (20) and a flexible sheet (28) (also called flexible membrane), as described by FIG. 7. The flexible sheet may be secured/sealed to the rigid part at a junction edge (for example by thermos, ultrasonic, infrared or laser-welding or gluing). Both define the first storage compartment (11a), in particular, the internal wall of the rigid part and of the flexible sheet. The rigid part (20) may comprise a concave internal structure (24) and the flexible sheet may be configured to come into contact with the internal wall of the rigid part (20), for example, the flexible sheet may be elastic and/or thermoformed.

The concave internal structure (24) is preferentially designed in such a manner that the dead volume of the first storage compartment (the residual volume at the end of the delivery) is minimal for example substantially equal to 0. For example, at the end of the treatment, the wall (of the concave internal structure (24)) intended to be in contact with the solution is covered by the flexible sheet and substantially in contact with the flexible sheet. Thus at the end of the treatment (end of delivery), the first container stores a residual volume of solution which is less than 10% of the solution initially stored in the first container, preferentially less than 8%, more preferentially less than 5%. Furthermore, at the end of the treatment (end of delivery), the delivery system comprises a residual volume of solution which is less than 10% of the solution initially stored in the first container, preferentially less than 8%, more preferentially less than 5%.

Furthermore, as described in FIG. 7a, the concave internal structure (24) may comprise a first angle β and a second angle α. The first angle β may be rounded with a strictly non-null radius of curvature and located close to the junction edge (43) and may initiate the concave internal structure. This angle must be larger than 90° and smaller than 180° in order to promote a substantially complete emptying of the container. The radius of curvature of this angle is meant to compensate misalignment/assembly tolerances of the rigid part of the container (20) and the flexible sheet (28). The second angle α may be rounded with a strictly non-null radius of curvature located close to a bottom of the container and may initiate a substantial bottom plate of the first container. This substantial bottom plate may comprise at least one of the outlet, the channel and the filter. The radius of curvature of the second angle α is meant to promote a substantial emptying of the container by allowing the flexible sheet (28) to come into contact with the concave internal structure (24) smoothly, without creases. At least one of the first angle β' and the second angle α' (preferentially both) of the flexible sheet and their respective radius of curvature may be substantially similar to α and β (preferentially equal), in such a manner that the internal wall of the flexible sheet may match as much as possible the internal wall of the concave internal structure.

Furthermore, as described in FIG. 7b, the concave internal structure (24) may comprise a first angle β and a second angle α. The first angle β may have a radius of curvature substantially null and located close to the junction edge (43) and may initiate the concave internal structure. This angle must be larger than 90° and smaller than 180° in order to promote a substantially complete emptying of the container. The second angle α may be rounded with a strictly positive radius of curvature located close to a bottom of the container and may initiate a substantial bottom plate of the first container. This substantial bottom plate may comprise at least one of the outlet, the channel and the filter. The radius of curvature of the second angle α is meant to promote a substantial emptying of the container by allowing the flexible sheet (28) to come into contact with the concave internal structure (24) smoothly, without creases. At least one of the first angle β' and the second angle α' (preferentially both) of the flexible sheet and their respective radius of curvature may be substantially similar to α and β (preferentially equal), in such a manner that the internal wall of the flexible sheet may match as much as possible the internal wall of the concave internal structure.

Furthermore, the flexible sheet may be thermoformed so as to have a substantially similar shape of the internal wall of the concave internal structure. The first container may further comprise a slope (P).

Thus, the shape and the characteristic of the concave internal structure and the flexible sheet may be configured to allow a substantial draining of the first storage compartment.

The second container (12) may comprise similar features to the first container (11).

As described by the FIG. 11, the rigid part (20) of the first container may comprise one or more channel (31), and/or a cavity (30) at the outlet location (32).

The cavity (30) and/or the channel (31) may be arranged in the internal wall of the rigid part (20) and may be configured to prevent clogging of the outlet by the flexible sheet before the end of the delivery.

In order to prevent the clogging of the outlet (before the end of the delivery), at least one of the first and the second containers may be configured to enable a collapse of the flexible membrane in a determined manner, in a determined direction (29) and/or in determined sequence. For example, the flexible membrane may collapse in a first instance to a remote location from the outlet and then the flexible sheet may collapse toward the outlet (of the container). As described by FIGS. 9a and 9b, the determined direction may be parallel to the length of the container.

Other examples of features which should prevent the clogging of the outlet (before the end of the delivery):
  the width of the rigid part (20) close to the outlet location may be narrower than the farthest part or parts from the outlet,
  the outlet location may be arranged close to a vertical wall/internal edge of the container,
  the outlet location may not be arranged at or close to the center of the container,
  the outlet location may be arranged as far as possible from the center of the container,
  the flexible membrane may be more flexible close to the first end,
  the flexible membrane may be less flexible at the outlet location,
  the flexible membrane may comprise a determined shape at the outlet location (for example an additional cavity),
  the thermoforming of the flexible membrane may be done such as to exhibit larger compliance far from the outlet and the smallest compliance around the outlet, and/or
  the thermoforming may be configured to limit the collapse at the outlet location.

FIG. 10 shows an example of a container (50) having a flexible wall (51) and an opposite wall (52). The opposite wall defines an internal cavity in which the flexible wall is configured to come into contact. The flexible wall may be thermoformed. The opposite wall may be flexible or rigid. The first part (53) of the flexible wall is thermoformed in such a manner to come in contact with a predetermined strain which is greater than the required strain for the second part (54) of the flexible wall. In other terms, the first part (53) of the flexible wall requires a plastic or elastic deformation of the flexible wall which is greater than the second part (54).

The material of the flexible membrane (single flexible membrane, first flexible membrane or second flexible membrane) may, for example, consist of one or more polymers of the following families: Polypropylene (PP), Polyethylene (PE), Ethylene Vinyl Alcohol (EVOH), Polyamide (PA), Polychlorotrifluoroethylene (PCTFE), Cyclic Olefin Copolymer (COC), Cyclic Olefin Copolymer elastomer (COC elastomer), Polycarbonate (PC), Ethylene Vynil Acetate (EVA), Polyvinyl Chloride (PVC), Polyvinylidene Chloride (PVDC), Polystyrene (PS), Polyethylene Terephthalate (PET), Thermoplastic Elastomer (TPE), Polymethacrylate (PMMA/MABS/MBS), Nitrile Butadiene Rubber (NBR), Natural Rubber (NR), Silicone, or other polymers. The flexible membrane may be thermoformed and may be manufactured for example by extrusion, blown film extrusion, coextrusion or lamination.

The rigid wall part may be an injection molded part. It may for example, consist of one or more polymers of the following families: Polypropylene (PP), Cyclic Olefin Copolymer (COC), Polymethacrylate (PMMA/MABS/MBS), Polyoxymethylene (POM), Acrylonitrile butadiene styrene (ABS), Copolyester (PCTG), Polyethylene Terephthalate (PET) or Polycarbonate (PC). Fillers can be used to reinforce the shell, e.g. glass fibers, Kevlar . . .

In order to reduce the cost of the rigid part of the container, the delivery system may comprise a first layer and a second layer. The first layer may comprise a first surface intended to be in contact with the solution and a second surface intended to be in contact with the second layer. Preferentially the first surface is arranged on another face (for example opposite face) than the face comprising the second surface. The second layer is intended to provide a determined mechanic property (for example a better rigidity) to the container. The first layer may be independent of (it may be removably coupled to) or secured to the second layer (for example rigidly fixed). In this case, the first layer may, for example, consist of one or more polymers of the following families: Polypropylene (PP), Cyclic Olefin Copolymer (COC), Polymethacrylate (PMMA/MABS/MBS), Copolyester (PCTG), Polyethylene Terephthalate (PET) or Polycarbonate (PC). And the second layer may for example, consist of one or more polymers of the following families: Polyethylene (PE, HDPE, LDPE), Polypropylene (PP), Polyethylene Terephthalate (PETE or PET), Acrylonitrile-Butadiene-Styrene (ABS), Polyvinyl Chloride (PVC), Polyamide (PA), Acrylic (PMMA), Polylactic Acid (PLA), Polycarbonate (PC), Polystyrene (PS, GGPS, HIPS), Acetal, Polyoxymethylene (POM), Polyurethane (PU) or glass fibres . . .

The first container (11) may comprise a rigid part and a flexible part as described by the US patent application US20140166528, the content of the patent application is incorporated by reference in the present document.

The second and the third container may be configured to store a compressible fluid (for example in a compressed state) such as a propellant, for example consisting of one or more material of the following families: butane, propane, CFC11, CFC12, CFC114, HFA 134a, HFA 152a, HFA 227, Isobutene, n-butane, HFO1234yf, or HFO1234ze. Thus the flexible membrane (single flexible membrane, first flexible membrane or second flexible membrane) may be configured to be in contact with a compressible fluid such as listed above. In this case, the material (which may be intended to be in contact with the compressed fluid (propellant)), for example, the second flexible membrane, may consist of one or more material of the following families: Natural Rubber, Styrene Butadiene, Ethylene Propylene (EPDM), Nitrile, Neoprene, Fluorocarbon, Fluoro Silicone, Urethane, SBR, Silicone, Butyl, Polyacrylate, Hypalon, Viton, Polyurethane, Fluorosilicone, Aflas, or Kalrez.

When the compressed fluid enters into the second storage compartment, the expansion of the compressed fluid induces shocks which may damage the flexible membrane of the first container or the solution. Thus, the second flexible membrane may be configured to insulate/protect the first flexible membrane and/or the solution from the thermal shock and/or expansion shock when the compressed fluid enters into the second storage compartment. An additional layer arranged between the first and the second flexible membrane may comprise a thermally insulating material.

At least one of the fluid compressed, the fluid pathway (5), the third container (13) and the second container (12) may be adapted to one or several features (volume, viscosity, active agent, life cycle, live time of the solution . . . ) of the solution stored in the first container in order to infuse the solution during a predetermined time period.

The second container may further comprise an outlet configured to drain the second storage compartment at the end of use or delivery. This outlet may be closed by a valve device during the delivery and when the first storage compartment has been drained, this valve device may be open (automatically or by a user).

The first, the second and/or the third container may be arranged into the housing. In one embodiment, the rigid part (or at least a part) of one of the containers may be a part of the housing of the delivery system. In other terms, a part of the rigid part of one of the containers may be configured to be in contact with the external environment of the delivery system. Thus, the mechanical property of the rigid part of the container is designed in such a manner to provide mechanical protection to the delivery system.

The housing may for example, consist of one or more polymers of the following families: Cyclic Olefin Copolymer (COC), Polymethacrylate (PMMA/MABS/MBS), Copolyester (PCTG), Polyethylene (PE, HDPE, LDPE), Polypropylene (PP), Polyethylene Terephthalate (PETE or PET), Acrylonitrile-Butadiene-Styrene (ABS), Polyvinyl Chloride (PVC), Polyamide (PA), Acrylic (PMMA), Polylactic Acid (PLA) Polycarbonate (PC), Polystyrene (PS, GGPS, HIPS), Acetal, Polyoxymethylene (POM), Polyurethane (PU) or glass fibers . . .

The rigid housing and/or at least a part of the container may be translucent or transparent and/or the rigid housing may comprise a window so as to see the container.

The rigid part of at least one of the first container (11) and the second container (12) may define a part of the housing (10) (which may be into contact with the external environment). At least a part of the rigid wall of the third container may be a part of the housing (10) (which may be into contact with the external environment).

Preferentially, the first container and the second container comprise symmetric forms at least in one dimension (for example length and/or width) in such a manner that the second flexible membrane substantially (preferentially perfectly) matches with the concave internal structure of the first container.

Preferentially, the first (resp. second) container or the housing/support of the first (resp. second) container may comprise edge and/or coupling devices (clip or screw or other fixing means) configured to rigidly fix (or to glue or to weld) to the second (resp. first) container or the housing/support of the second (resp. first) container and/or to the third container or the housing/support of the third container.

1.6 Containers Arrangement

Preferentially the first container is adjacent to the second container, more preferentially, the first movable wall is opposite to the second movable wall in such a manner that the first and the second movable walls may be in contact and in pressure communication.

Figure 3A:
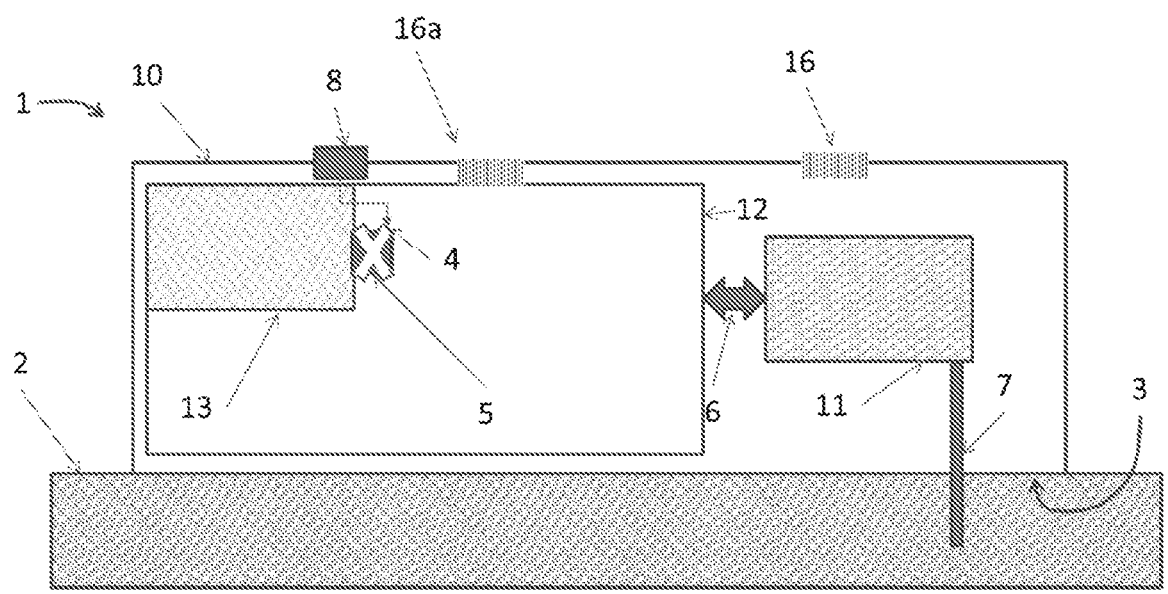
FIGS. 3a and 3b show schematic views of the general structure with two distinct arrangements of the second and third containers.
Figure 3B:
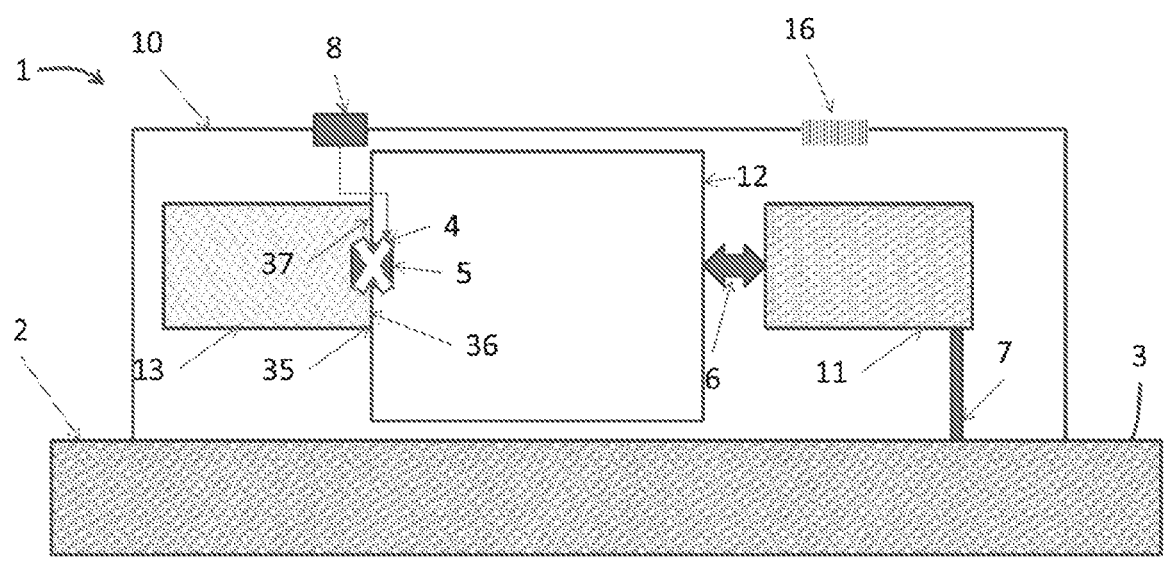

As disclosed by FIG. 3a, the third container (13) may be arranged at least partially into the second storage compartment. As disclosed by the FIG. 3b, at least a part of the rigid wall (35) of the third container (13) may be at least a part of the rigid wall of the second container (12). In other terms, a first surface (36) of a rigid wall (35) defines a part of the second storage compartment and a second surface (37) of the same rigid wall (35) defines a part of the third storage compartment. The first surface (36) may be opposite to the second surface (37).

In one embodiment, at least one rigid part of one of the containers is used as a rigid structure of the delivery system. In this case, the other elements of the delivery system may be secured to this rigid part (for example another container, housing, indicator device, transcutaneous device, skin-adherable unit).

In one embodiment as described by the FIG. 12, the first container (101) and the second container (102) are arranged into a cavity defined by a rigid housing which may include at least one of a first rigid housing (131) and a second rigid housing (132). The rigid housing may comprise one or more vents (141) configured to insure pressure equilibrium between the cavity (140) and the external environment of the delivery system (100) when at least one of the first storage compartment volume and the second storage compartment volume changes. The first rigid housing (131) may comprise a part of a first fluid pathway (142) in which the solution flow or passage in which said first fluid pathway is arranged. The second rigid housing (132) may comprise a part of a second fluid pathway (143) in which the compressed fluid flow or passage in which said second fluid pathway is arranged.

The first rigid housing may comprise a concave internal structure configured to receive at least a part of the first container (101). The first container (101) may be secured to the first rigid housing (131). At least a part of the concave internal structure of the first rigid housing may be formed so as to match with a part of the external surface of the first container.

The third container (103) (or the housing comprising the third storage compartment) and/or the indicator device (104) may be secured to the rigid housing (131, 132).

The first container may be a first flexible pouch configured to be in fluid communication with the transcutaneous device and the second container may be a second flexible pouch configured to be in fluid communication with the third container. In this case, the edge of the flexible pouch may be rigidly fixed to the housing at least at two separate locations.

FIG. 13 shows an exploded view of a container (the first or the second container) and a part of the housing. The container (200) comprises a flexible membrane (201) sealed on a rigid part (202) and both define the storage compartment. The container further comprises a fluid pathway (206) in fluid connection with the storage compartment. The rigid housing (203) is configured to improve the mechanical property of the rigid part (202) of the container. The rigid housing (203) comprises a concave internal structure (208) fitted to at least a part of the external surface (209) of the container. The rigid housing may further comprise one or more vent (204) and passage (205) for the fluid pathway (206). The passage may be at least partially covered by a lid (207) or also used as a vent.

The rigid housing and/or at least a part of the container may be translucent or transparent and/or the rigid housing may comprise a window so as to see the container.

FIG. 14 shows an exploded view of a container (300) (the first or the second container). The container (300) comprises a flexible membrane (301) sealed on a rigid part (302) and both define the storage compartment. The rigid part may further comprise a protrusion (308) having one or more vent (306) and/or support (305) configured to seal/fix the edge (304) of the flexible membrane. The support (305) may be a groove, a slot, a rim, an edge and/or a sill of the rigid part (302). The protrusion (308) may extend along a peripheral edge of the cavity (of the container interface) and/or toward an opposite container. The container further comprises a fluid pathway (303) in fluid connection with the storage compartment.

At least a part of the external surface (307) of the rigid part (302) may be a part of the housing.

At least a part of the external surface (307) of the rigid part (302) may be a rigid structure or a frame configured to secure/attach on it other elements of the delivery system such as another container, indicator device, transcutaneous device and/or skin-adherable unit.

Figure 2:
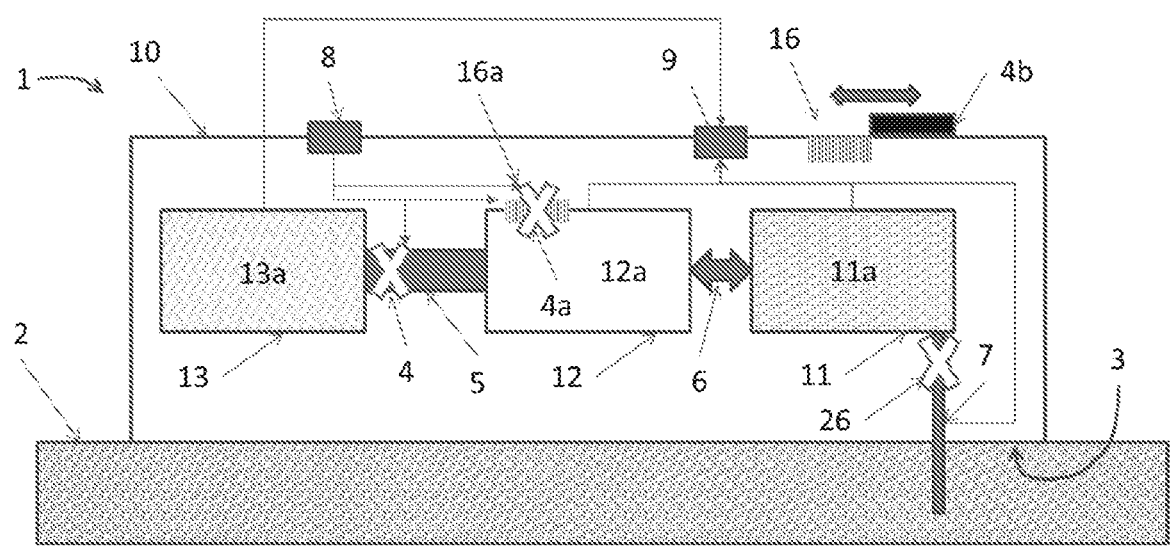
FIG. 2 shows a schematic view of the general structure according to an embodiment.

According to FIGS. 2 to 4, the containers may be arranged side by side.

The delivery system may comprise a proximal part and a distal part (to the patient skin). Preferentially, the proximal part comprises a lower face and may be configured (for example at least a part of the lower face) to be coupled to the skin-adherable unit or to be secured to the patient skin. The distal part comprises upper face and at least a part of the distal part (for example at least a part of the upper face) is configured to be visible (by the patient or other persons) when the delivery system is fixed on the patient skin.

Figure 17A:
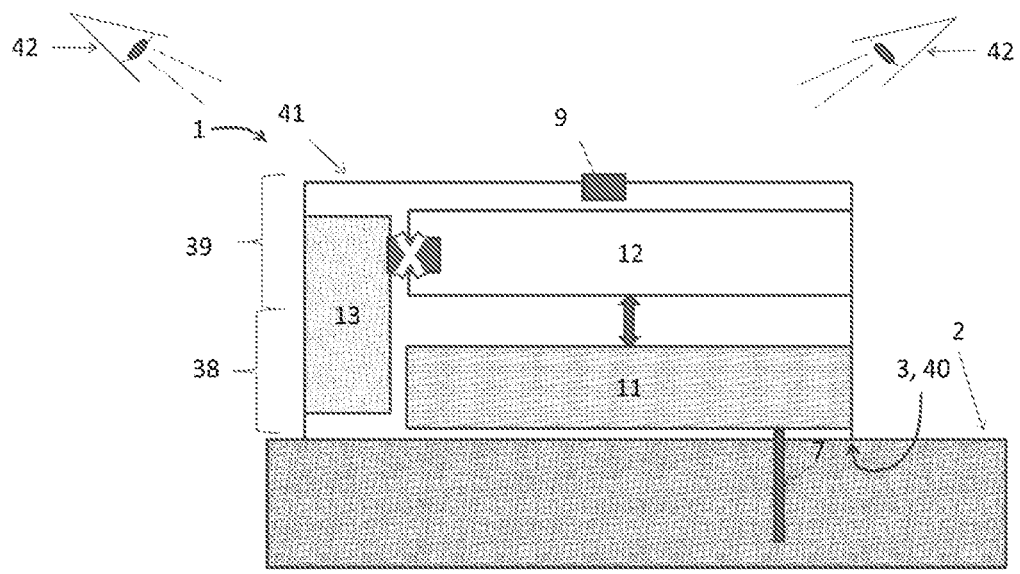
Figure 17B:
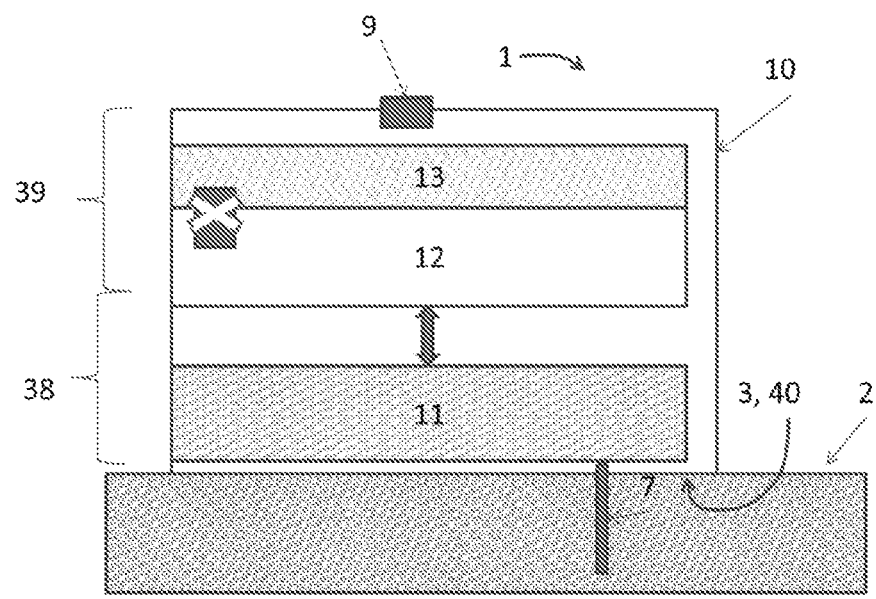

According to the FIGS. 17a and 17b, the first container (11) is arranged at least partially in the proximal part (38) in order to simplify the fluid pathway connected to the injection device (7) and the second container (12) is arranged above the first container (11) for example at least partially in the distal part (39) of the delivery system (1). In this case, the third container (13) may be arranged above the second container (12) (as shown by the FIG. 17b) or on the side of at least one of the first container and the second container (as shown by the FIG. 17a). At least a part of the first container (for example a rigid part of the first container) forms/defines the lower face of the delivery system and may be secured or coupled to the skin-adherable unit. At least a part of the second and/or third container (preferentially a rigid part) may form/define the upper face of the delivery system. Preferentially, at least a part of the proximal part may comprise a window or a translucent or transparent material so to see the solution stored into the first container.

Figure 17C:
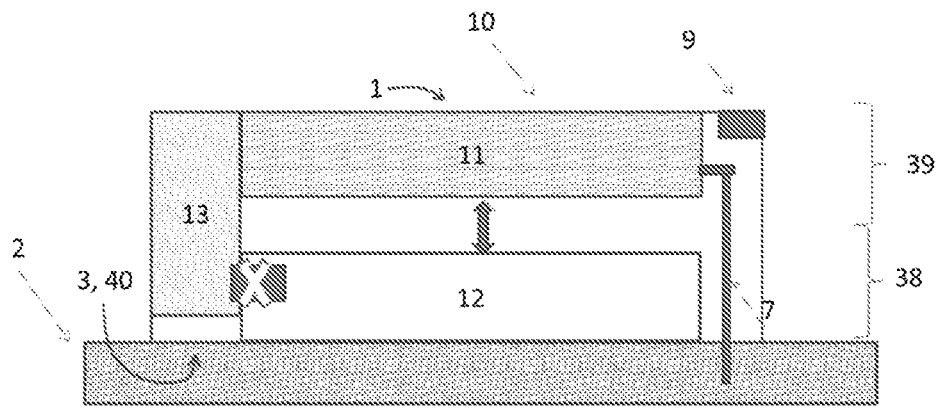
Figure 17D:
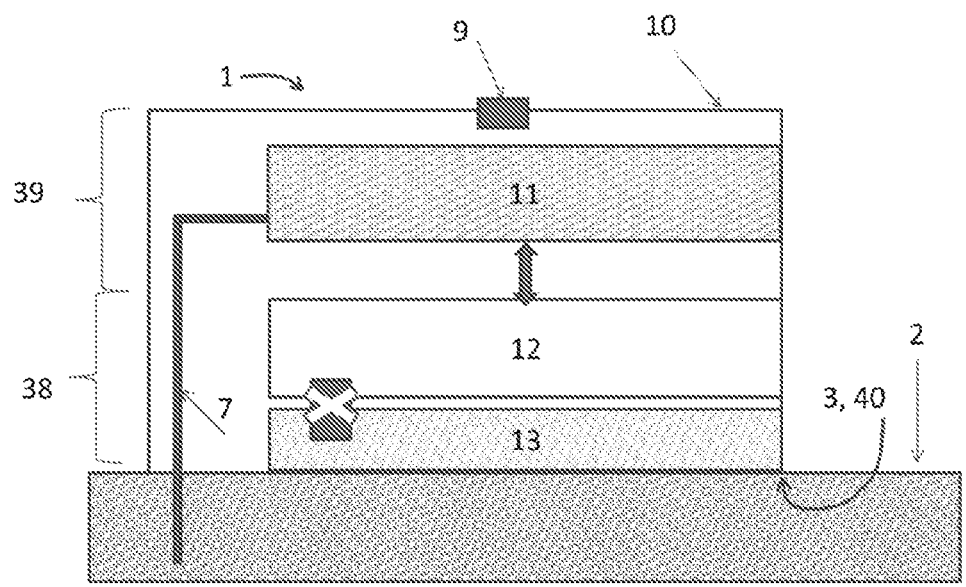

According to the FIGS. 17c and 17d, the second container (12) is arranged at least partially in the proximal part (38) and the first container (11) is arranged above the second container (12) for example at least partially in the distal part (39) of the delivery system (1). In this case, the third container (13) may be arranged below the second container (12) (as shown by the FIG. 17d) or on the side of at least one of the first container and the second container (as shown by the FIG. 17c). At least a part of the first container (for example a rigid part of the first container) may form/define the upper face of the delivery system. At least a part of the second and/or third container (preferentially a rigid part) forms/defines the lower face of the delivery system and may be secured or coupled to the skin-adherable unit. Preferentially, at least a part of the distal part may comprise a window or a translucent or transparent material so as to see the solution stored into the first container, even if the delivery system is secured on the patient skin.

The indicator device (9) is preferentially arranged in such a manner to be visible to the patient when the delivery system is secured on to the patient skin, for example, the indicator device may be arranged in the upper area of the delivery device FIGS. 17a, 17b, and 17d) or in the upper, lateral area of the delivery system (FIG. 17c).

1.7 Examples Of Embodiments

Figure 12C:
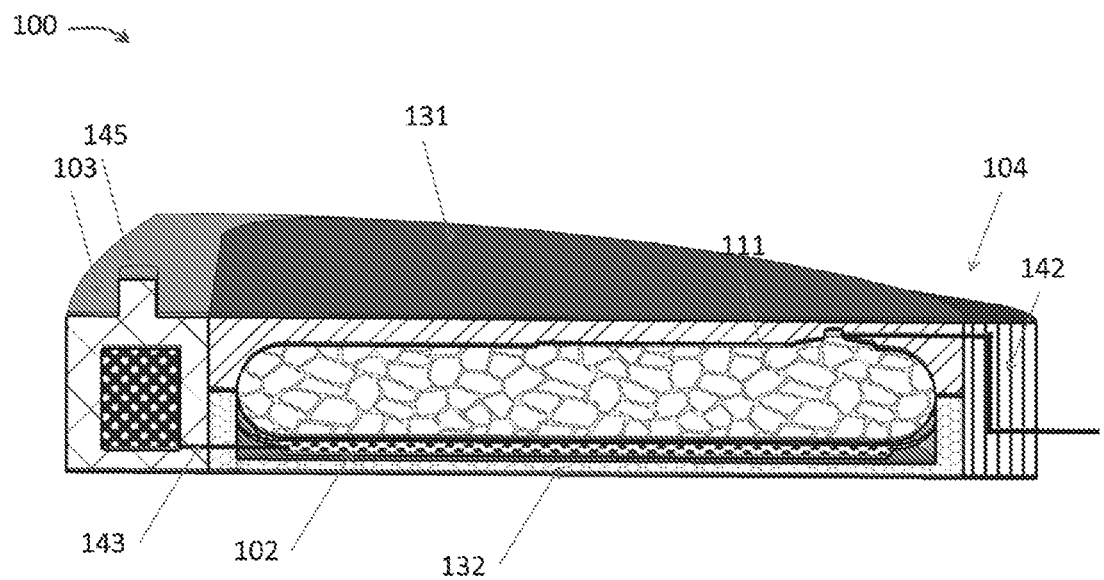
Figure 12D:
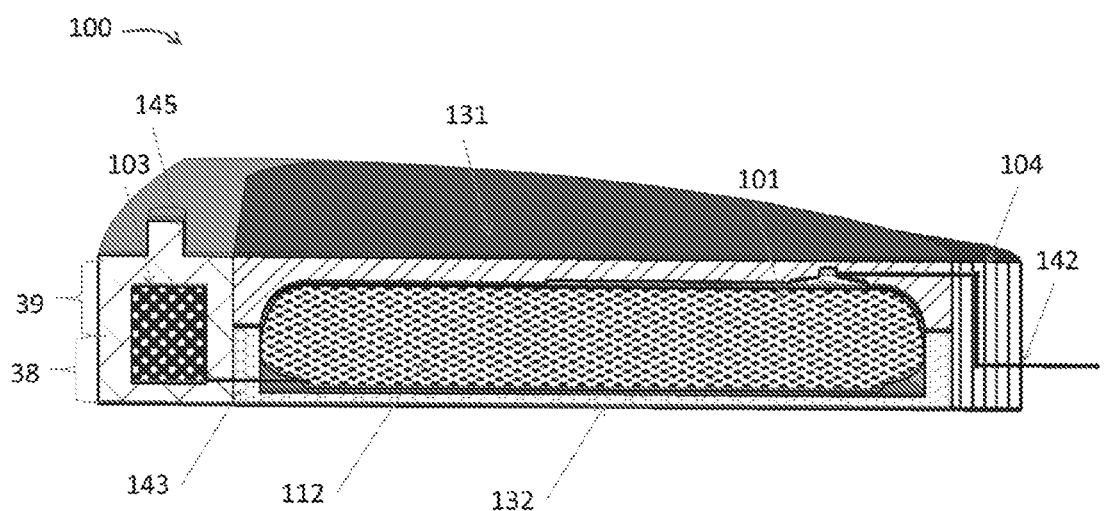

According to the FIGS. 12a to 12d 12b, the delivery system (100) comprises a first container (101), a second container (102) and a third container (103). The first container (101) comprises a first storage compartment (111) intended to store a solution (FIG. 12c). The second container (102) comprises a second storage compartment (112) intended to receive a propellant when the delivery system (100) is in the delivery state (FIG. 12d). The first container (101) comprises a first flexible membrane (121) and the second container (102) comprises a second flexible membrane (122). The first flexible membrane (121) is arranged opposite the second flexible membrane (122). The first container and the second container are configured to be in pressure communication when the first flexible membrane and the second flexible membrane are in contact. The pressure transmission may be partial or total and may depend on the elasticity of at least one of the first and the second flexible membranes.

In FIG. 12a, the first storage compartment (111) and the second storage compartment (112) are substantially empty.

The first storage compartment (111) is configured to be in fluid communication with a patient via a first fluid pathway (142) and optionally via a transcutaneous device (not shown). The second storage compartment (112) is configured to be in fluid communication with the third container (103) via the second fluid pathway (143).

The delivery system (100) may further comprise an indicator device (104) which may be in fluid or pressure communication with the first storage compartment (111), preferentially before the main fluidic resistance of the fluid pathway, for example before the flow resctrictor. The delivery system (100) may further comprise a trigger device (145) configured to launch/initiate a delivery sequence. The delivery sequence may comprise a delivery step and an optional countdown step (before the delivery).

At least one of the first flexible membrane (121) and the second flexible membrane (122) defines the cavity of the containers' interface. The cavity (140) is vented by at least one vent (141).

The first container (101) may be arranged at least partially in the distal part (39) of the delivery system (100) and the second container (102) may be arranged at least partially in the proximal part (38) of the delivery system (100).

The FIG. 12c shows the same delivery system (100) but with a first container (101) filled with the solution. And the FIG. 12d shows the delivery system (100) with a first container (101) drained and a second container (102) filled with the compressed fluid.

The FIGS. 15a and 15b show another embodiment where at least one of the first container (401) and the second container (402) comprises a butterfly shape. The first container (401) and the second container (402) comprise symmetric forms at least in one dimension (for example length and/or width) in such a manner that the second flexible membrane (422) substantially (preferentially perfectly) matches with the internal wall of the rigid part (451) of the first container (401). Preferentially, the inlet (447) of the second container is not arranged above/below the outlet (446) of the first container.

The delivery system comprises a first container (401) and a second container (402), both arranged opposite each other. The first container may comprise a rigid part (451) and a part of the rigid part (451) may act as a first rigid shell (431) of the delivery system (400). The second container may comprise a rigid part (452) and a part of the rigid part (452) may act as a second rigid shell (432) of the delivery system (400).

The delivery system may further comprise a third container (403) and a trigger device (445) arranged on the side of at least one of the first container (401) and the second container (402).

The delivery system may further comprise an indicator device (404) arranged on the side of at least one of the first container (401) and the second container (402).

The first rigid shell (431) may comprise a surface configured to be coupled or to be secured to a skin adherable unit (not shown). The indicator device may comprise visible information (LED, Message, level indicator) arranged on a visible part of the delivery system (400) when the delivery system is secured on the patient skin.

At least a part of the second rigid shell (432) may comprise an upper face of the delivery system (400).

The FIGS. 16a and 16b show a delivery system (400) having a substantial egg shape. In the embodiment of FIG. 16a, the containers are stacked on top of each other. In the embodiment of the FIG. 16b, at least one of the first container (401) and the second container (402) comprises one or more vent (441). The first container may be arranged at least partially into a first rigid shell (431). The second container (402) may comprise a rigid part (452) having a surface configured to form or define at least a part of the rigid shell (432).

The FIG. 18 shows a 3d view of a potential embodiment wherein the injection may be driven by (for example) a liquefied gas reservoir (arranged into the housing (10)) that is opened by the user after placement onto the patch (not shown). Examples of patches have been described by the U.S. Pat. No. 9,833,565 and the EP patent application EP18200265.9, the contents of which are incorporated by reference in the present application. As explained above, the vapourization of the liquefied gas may generate a large pressure differential that will push the elastomeric membrane against the flexible part of the drug reservoir. The cavity between the two membranes may be vented by the first venting element (16) to prevent any risk of infusion of propellant into the patient. The pressure acting on the fluid is equal to the vapor pressure of the propellant since both membranes are flexible. At the bottom of the drug reservoir, a small cavity may be used to connect at least one of an infusion status indicator, a filling indicator, and/or the fluid restriction used to limit the flow rate to a maximum of 1.5 mL/min.

Figures 19A, 19B, 19C:
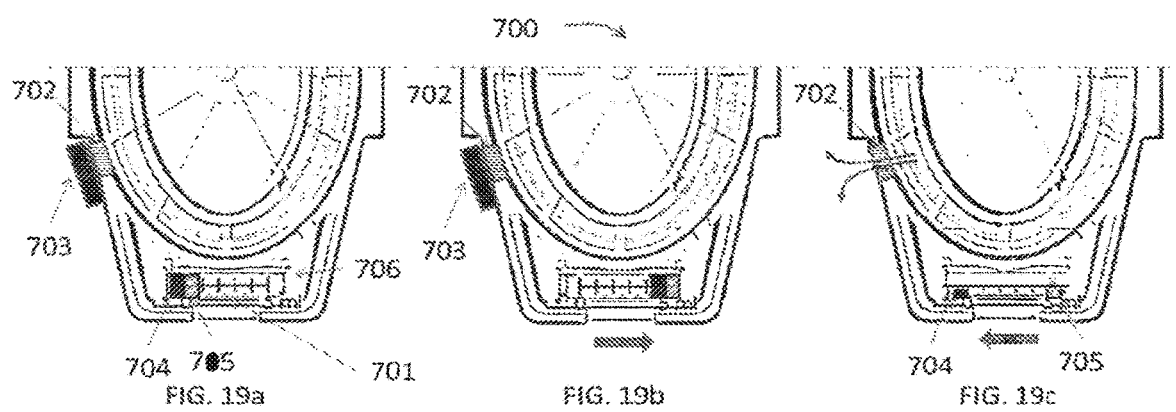

The FIG. 19 show several views of a potential filling indicator (701) (or filling gauge) which may be used with the system (700) described in this document. An example of a filling indicator has been described by the EP patent application EP18215745.3 and EP19151325.8, which are incorporated by reference in the present application. As described above, the system may contain a first container comprising a flexible membrane that may be initially collapsed against a rigid part, and user-filled with a syringe. This action inflates the flexible membrane, which may be thermoformed to prevent the generation of pressure onto the drug as the filling is completed. The cavity of the containers' interface may be not vented during the filling process for example the first venting element (702) of the cavity may be occluded by a valve device (703) (such as a plug, . . . ). In this case, during filling, a positive pressure generated inside the containers' interface cavity will move one or more plungers (704, 705) (for example two plungers) inside a transparent cylinder (706), equilibrating the pressure inside the container (as shown FIG. 19b). The filling indicator may be located on the bottom of the device and/or may be only visible during the filling process. As shown in the FIGS. 19a, b, and c, the fill volume is indicated by the position of the one or more plungers (704, 705). The FIG. 19a shows two plungers (704, 705) at the left of the indicator, before the filling. The FIG. 19b shows two plungers at the right of the indicator and indicates the current fill volume, just after the filling before to disable the valve device (703) from the first venting element. The FIG. 19c shows a first plunger (704) at the left of the indicator and a second plunger (705) at the right, after the valve device disable (open or removed). A textual indication or gradual indication may indicate the fill volume by the second plunger (705).

Figures 20A, 20B, 20C:
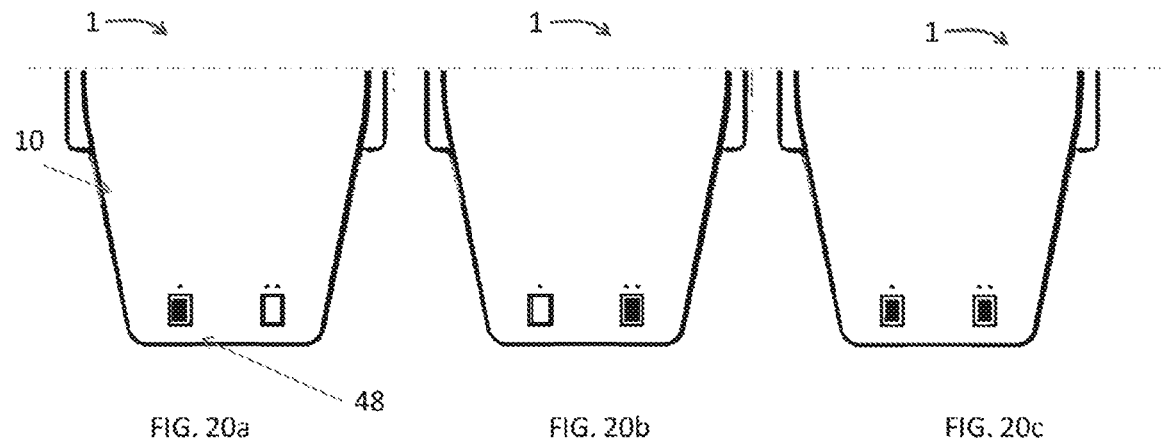

The FIG. 20 show several external views of a potential infusion status indicator (2) which may be used with the system described in this document. An example of an infusion status indicator has been described by the EP patent applications EP18157250.4, EP19151323.3 and international patent application PCT/IB2019/051237, which are incorporated by reference in the present application. The system (1) may comprise a housing (10) having one or more windows and at least a part of the infusion status (or plunger of the indicator) indicator may be arranged in the vicinity to the window. The housing may comprise textual indication or other indication (color, symbol, . . . ) near the windows to indicate status. The infusion status indicator may comprise a transparent cylinder that contains one drilled plunger and another solid one in contact with the drug (in this document "solid" may be understood as opposed to drilled). The pressure generated during infusion first moves both plungers towards the dead-end of the cylinder until pressure equilibration. When the full dose has been administered, the reservoir membrane can no longer transmit the propellant pressure to the fluid (the drug) and therefore the solid plunger comes back to its initial position, infusing the residual amount of drug that was located inside the indicator cylinder. The dead volume of the device is thus limited to a few tens of a microlitre. FIG. 20 show a first illustrative version of this indicator as seen on the top shell of the device (for example). This purely mechanical infusion status indicator may have at least one of the following three different states:

One dot: Ready to inject (FIG. 20*a*),
Two dots: Injection on-going (FIG. 20*b*)
Three dots: End of injection (FIG. 20*c*).

The "end of injection" indication may be only visible when the reservoir membrane is fully collapsed against the bottom of the reservoir shell. It is not visible in case of cannula occlusion. For a specific medication volume and viscosity, maximum infusion duration will be indicated in the user manual, therefore the user can deduce that the full volume has not been administered (in case of total occlusion for instance) if the infusion status indicator is still showing "injection on-going" after this maximum duration. The high pressure generated by the propellant vapor will limit the occurrence of an occlusion in the cannula.

Figure 24A:
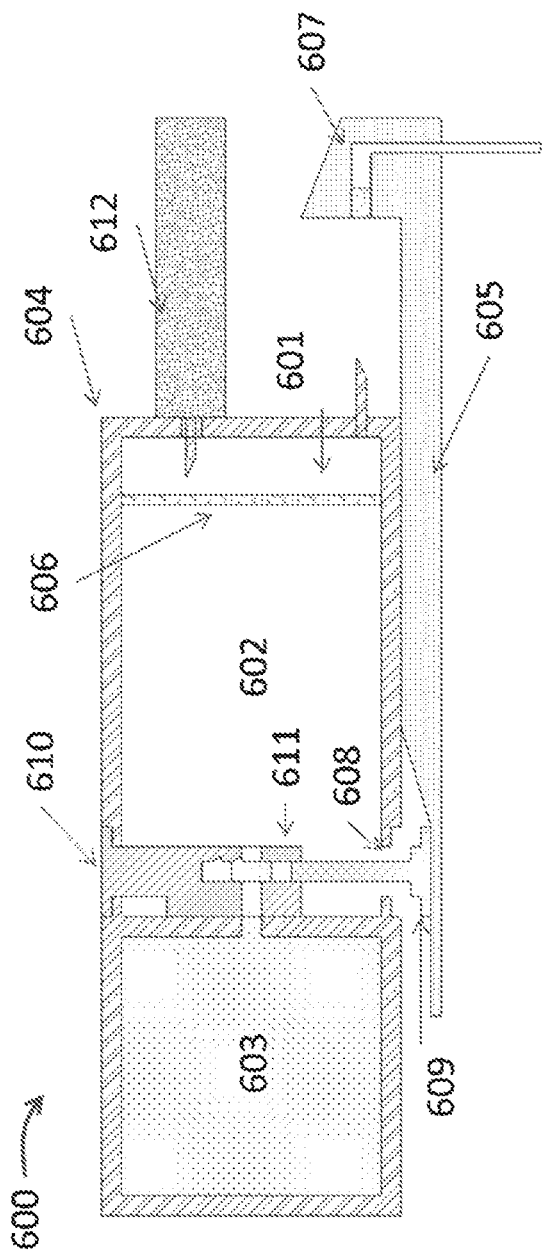

The FIGS. 24*a*, *b*, *c*, and *d* illustrate an embodiment comprising similar features disclosed above. The FIG. 24*a* shows some embodiments of a potential delivery system (600) with the numerical reference.

The delivery system (600) comprises a medical device (604) having a first container (601), a second container (602) and a third container (603). As disclosed in this document the third container may comprise a rigid wall adapted to store the propellant. The first and the second container may comprise a movable wall (606). In order to simplify the description, the interface between the first and the second container is called the movable wall (606) but it may be substituted by other features described in this document. For example, as described in this document, the movable wall (606) may comprise a first flexible membrane and a second flexible membrane, both defining at least a part of the containers' interface which may be vented by a vent device (not shown in FIG. 24).

Preferentially, the delivery system (600) comprises a cradle unit (605) configured to fix the medical device (605) to the patient skin and a transcutaneous device (607) (which may be a part of the cradle unit) intended to allow the infusion of the solution stored in the first container to the patient.

Preferentially, the delivery system (600) comprises a second venting element (608) configured to provide fluid communication of the second container to the outside of the delivery system (to the ambient air for example). The second venting element may be selectively open or closed via a first valve device (609) which may be a part of the cradle unit (605) or the medical device (604).

The first container is configured to store a medical solution intended to be infused to a patient. In the case where the first container is initially empty (for example delivered or sold empty), the first container may be configured to be filled with the solution before use via for example a cartridge (612).

The delivery system may further comprise a trigger device (610) configured to allow or provide fluid communication between the third container (603) and the second container (602) when the delivery system is activated.

The trigger device may be operatively coupled with a second valve device (611) configured to allow or provide fluid communication between the third container (603) and the second container (602) when the first valve device (609) is closed and/or the trigger device (610) triggered or activated.

Figure 24B:
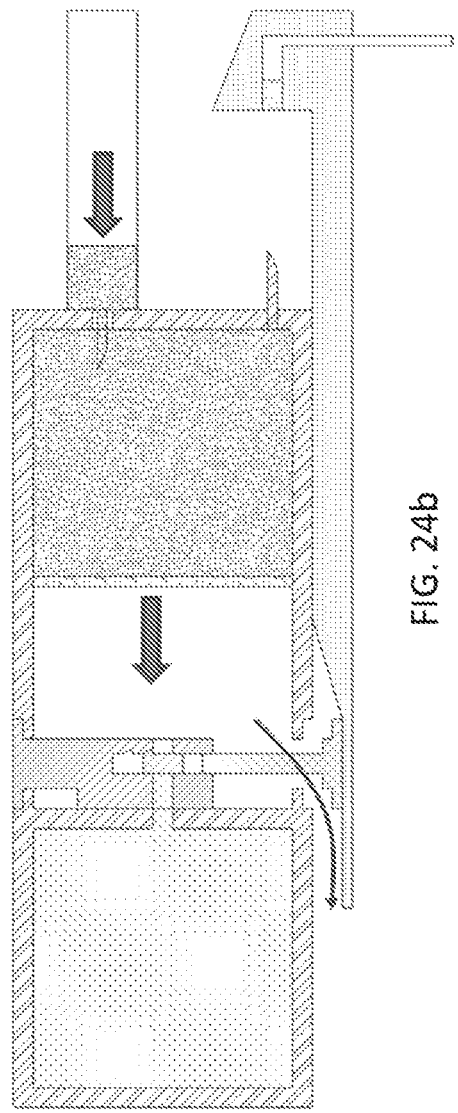

FIG. 24*b* illustrates the filling of the first container. Here, the medical solution is moved from the cartridge to the first container. The movable wall is moved as the first container is filled and during this process, the second container may be vented. If the movable wall comprises a first and second flexible membrane defining a cavity, a first venting element may be configured to vent the cavity during this process.

FIG. 24*c* shows the cradle unit fixed on the patient skin. The medical device is moved from a first position to a second position (relatively to the cradle unit or to the patient skin). As a result, a needle pierces a septum so as to provide fluid communication between an outlet port of the medical device and the transcutaneous device and the first valve device closes the second venting element. In some embodiments, the trigger device may be configured to be armed when the first valve device closes the second venting element or when the medical device is moved from a first position to a second position. For example, a button (of the trigger device) is moved out of the plan of the housing such that the user can activate the delivery system (or can trigger the trigger device).

FIG. 24*d* illustrates the activation of the delivery device. The trigger device is triggered and the second valve device opens the fluid pathway between the third container and the second container. Consequently, the pressure increases onto the second container and moves the movable wall causing the infusion of the medical solution to the patient.

In the end, when the medical device is removed from the patient or from the cradle unit, the second venting element may expel the gas stored in the second container, for example, the first valve may be opened.

The invention claimed is:

1. A delivery system configured to deliver medical fluid to a patient, the system comprising:
    a medical device including,
        a first container having a first storage compartment configured to store the medical fluid and having a first variable volume,
        a second container having a second storage compartment having a second variable volume, a third container having a third storage compartment configured to store a propellant, and
a container interface configured to operatively couple the first container and the second container such that a volume increase of the second variable volume induces a volume decrease of the first variable volume, the container interface including
a first movable wall of the first container,
a second movable wall of the second container, and
a cavity defined by at least the first and the second movable wall;
a skin adherable unit configured to secure the medical device to the patient skin;
a first valve device including,
a first position configured to prevent a fluid communication between the second storage compartment and the third storage compartment, and
a second position configured to allow a fluid communication between the second storage compartment and the third storage compartment such that the propellant stored in the third storage compartment may flow to the second storage compartment to increase the second variable volume; and
a vent device configured to prevent an unintended pressure increase in the first storage compartment.

2. The delivery system according to claim 1, wherein at least one of the first movable wall and the second movable wall include a flexible membrane.

3. The delivery system according to claim 1, wherein the cavity of the container interface includes a third variable volume,
wherein the vent device includes a first venting element configured for pressure equilibration between the cavity of the container interface and an outside of the delivery system.

4. The delivery system according to claim 3, wherein the vent device includes a second venting element configured to allow a pressure equilibration between the second storage compartment and an outside of the delivery device.

5. The delivery system according to claim 4, further comprising: a second valve device configured to at least partially occlude the second venting element.

6. The delivery system according to claim 5, wherein the first valve device and second valve device are operatively coupled such that when the second valve device does not occlude the second venting element, the first valve device is in the first position, when the second valve device occludes the second venting element, the first valve device is movable from the first position to the second position, and/or when the second valve device occludes the second venting element, the first valve device is automatically moved from the first position to the second position.

7. The delivery system according to claim 5, further comprising: a trigger device configured to change the position of the first valve device.

8. The delivery system according to claim 7, wherein the second valve device and the trigger device are operatively coupled such that when the second valve device does not occlude the second venting element, the trigger device is not in operating condition, and/or when the second valve device occludes the second venting element, the trigger device is in operating condition.

9. The delivery system according to claim 1, wherein the medical device comprises a first position and a second position.

10. The delivery system according to claim 9, wherein the vent device includes a venting element configured to allow a pressure equilibration between the second storage compartment and an outside of the delivery device,
the delivery system further comprising a second valve device configured to at least partially occlude the venting element,
wherein the medical device is operatively coupled to at least one of the first valve device, the second valve device, the trigger device, and the skin adherable unit such that, when the medical device is in a first position, the second valve device does not occlude the venting element, when the medical device is in the first position, the trigger device is not in operating condition, when the medical device is in a second position, the second valve device occludes the venting element, when the medical device is in the second position, the trigger device is in operating condition, and when the medical device is in the second position, the first valve device is movable from the first position to the second position, and/or when the medical device is in the second position, the first valve device is automatically moved from the first position to the second position.

11. The delivery system according to claim 1, further comprising: a countdown mechanism configured to activate the trigger device after a predetermined time period.

12. A delivery system configured to be secured on a patient skin comprising:
a first container having a first movable wall and a first storage compartment configured to store a medical fluid;
a second container having a second movable wall and a second storage compartment; and
a skin adherable unit configured to secure the first container and the second container to the patient skin;
wherein the first movable wall and the second movable wall are facing each other and define a container interface having a cavity; and
a vent device configured to allow a pressure equilibration between the cavity of the container interface and ambient air surrounding the delivery system when at least one of the first movable wall and the second movable wall moves.

13. The delivery system according to claim 12, wherein the first container and the second container are in pressure communication when the first movable wall and the second movable wall are at least partially in contact.

14. The delivery system according to claim 12, wherein the cavity of the container interface comprises a variable volume depending on the movement of at least one of the first movable wall and the second movable wall.

15. The delivery system according to claim 12, further comprising: a third container configured to store a propellant in a third storage compartment.

16. The delivery system according to claim 15, further comprising: a fluid pathway and a fluid communication device configured to allow fluid communication between the third storage compartment and the second storage compartment when the fluid communication device is in an open position.

17. The delivery system according to claim 16, wherein the fluid communication device further comprises a second position configured to prevent the fluid communication between the second storage compartment and the third storage compartment.

18. The delivery system according to claim 12, further comprising: a trigger device operably coupled with the fluid communication device and configured to change the position of the fluid communication device.

* * * * *